United States Patent
Brainard

(10) Patent No.: US 8,404,795 B2
(45) Date of Patent: Mar. 26, 2013

(54) PHOTOLYTIC ACID-GENERATING POLYMERS AND MONOMERS FOR THEIR CONSTRUCTION

(75) Inventor: Robert L. Brainard, Albany, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 0 days.

(21) Appl. No.: 12/869,308

(22) Filed: Aug. 26, 2010

(65) Prior Publication Data

US 2011/0130538 A1 Jun. 2, 2011

Related U.S. Application Data

(60) Provisional application No. 61/237,158, filed on Aug. 26, 2009.

(51) Int. Cl.
*C08G 73/00* (2006.01)

(52) U.S. Cl. ........ 528/170; 528/174; 528/290; 528/391; 548/423; 548/433; 548/461; 548/462; 548/475; 548/523; 548/547

(58) Field of Classification Search .................. 528/170, 528/174, 290, 391; 548/423, 433, 461, 462, 548/475, 523, 547
See application file for complete search history.

(56) References Cited

U.S. PATENT DOCUMENTS 5,039,596 A 8/1991 Wu et al.

FOREIGN PATENT DOCUMENTS

WO 2009105667 8/2009

OTHER PUBLICATIONS

U.S. Appl. No. 12/918,647, filed Aug. 20, 2010 (Not yet published).
U.S. Appl. No. 12/869,220, filed Aug. 26, 2010 (Not yet published).
U.S. Appl. No. 12/869,202, filed Aug. 26, 2010 (Not yet published).
Se Young Oh et al. Synthesis and Resist Evaluation of Photosensitive Polyimides, Mol. Cryst. Liq. Cryst, 2000, vol. 349 (95-98).

*Primary Examiner* — Shane Fang
(74) *Attorney, Agent, or Firm* — Heslin Rothenberg Farley & Mesiti P.C.

(57) ABSTRACT

Polymers for photoresists and monomers for incorporation into those polymers are disclosed. The polymers comprise a photoacid generator (PAG) component and at least a second component that is photolytically stable and acid-stable. The polymers may also contain a third, acid-labile component. The photoacid generator is based on N-sulfoxyimides and related moieties that contain photolabile oxygen-heteroatom and oxygen-aromatic carbon bonds.

4 Claims, No Drawings

PHOTOLYTIC ACID-GENERATING POLYMERS AND MONOMERS FOR THEIR CONSTRUCTION

CROSS REFERENCE TO RELATED APPLICATIONS

This application claims benefit from U.S. Provisional Application 61/237,158 filed Aug. 26, 2009. The entire contents of the prior application are incorporated herein by reference.

FIELD OF THE INVENTION

The invention relates to polymers for photoresists and to monomers for incorporation into those polymers. The polymers comprise a photoacid generator (PAG) component and at least a second component that is photolytically stable and acid-stable. The photoacid generator is based on N-sulfoxyimides and related moieties that contain photolabile oxygen-heteroatom bonds or photolabile bonds between oxygen and aromatic carbons.

BACKGROUND OF THE INVENTION

Extreme Ultraviolet (EUV, 13.5 nm) imaging technology continues to be the primary option for the 22 nm microelectronics node. However, EUV resist performance remains one of the largest barriers to EUV technology implementation, because it is difficult to simultaneously meet performance targets for resolution, line width roughness (LWR) and sensitivity. For example, low concentrations of acid during imaging will yield rough lines (high LWR), but good sensitivity; high concentrations of acid will give smoother lines, but poor sensitivity. To break through to a new level of performance, new materials must be developed that will make improvements toward one performance target without compromising the performance of the other two.

Photoacid generators have been known in the polymer art for decades. Typical first-generation ionic PAGs are sulfonium and iodonium salts. In an early approach to a deep ultraviolet (DUV or 248 nm) photoresist or a 193 nm photoresist, the PAG is randomly dissolved within the polymer film. The polymer has an ester with a side-chain blocking group (e.g. t-butyl) that can be removed with catalytic acid, yielding a developer-soluble carboxylic acid. The advantage of this approach is that these resists are relatively inexpensive and simple to prepare using standard formulation methods. The resists have high sensitivity because acids are free to diffuse through the film, catalyzing acidolysis reactions (removal of ester blocking group) with large turnover numbers. The disadvantage of this approach is that the acid's rapid diffusion limits the ultimate resolution that can be achieved because the acid can diffuse into the unexposed regions of the resist—blurring the aerial image. In a second approach, for which the monomers of the present invention are useful, the photogenerated acid is bound into the polymer chain. The advantage of this approach is that the resist's resolution will not be limited by acid diffusion. A third approach, for which the monomers of the present invention are also useful, is described in PCT application PCT/US09/34707, filed Feb. 20, 2009. This application describes a resist system based on a polymer with PAG and ester functionality located within the main polymer chain. When the PAG breaks apart photochemically or the ester-linkages break apart by acidolysis, the molecular weight of the polymer decreases, allowing for higher acid diffusion during bake and faster resist dissolution during development. The polymer of PCT/US09/34707 is referred to as a chain scission polyester PAG-polymer (CSP$^3$). With CSP$^3$ the photochemical reaction breaks the polymer chain and produces a polymer-bound acid at a chain end. Then, the photogenerated acid catalyzes the transformation of the ester to the developer-soluble carboxylic acid by once again breaking the polymer chain. The resulting areas of the resist exposed to light and subjected to acidolysis reactions have much lower molecular weight resulting from the chain scission reactions. This provides lower Tg, higher acid diffusion rates, and faster dissolution rates.

SUMMARY OF THE INVENTION

In one aspect, the invention disclosed herein relates to a polymer comprising at least a first component and a second component. The first component is photolytically stable and acid-stable. The second component is chosen from units of the formulae

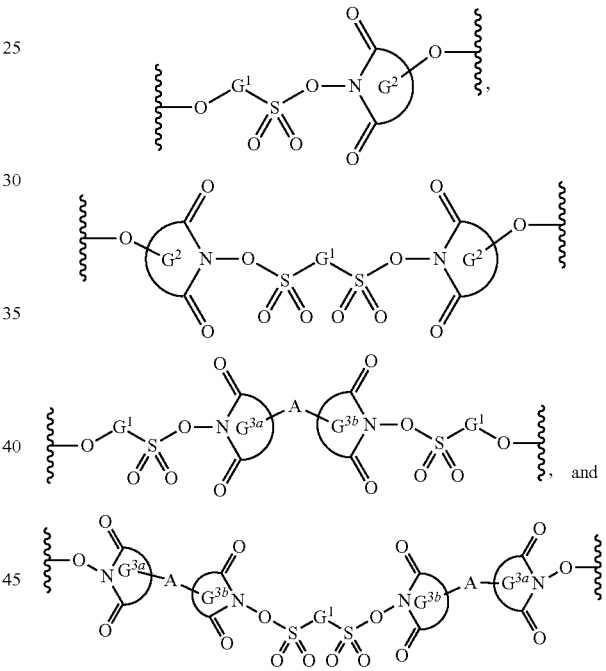

wherein $G^1$ is selected from an alkane, a fluoroalkane, an arene, a fluoroarene, a benzyl, a fluorobenzyl, a diaryl ether and a diaryl;

$G^2$ is an imide of empirical formula $C_{4-20}H_{3-12}N_{1-2}O_{2-5}$;

$G^{3a}$ and $G^{3b}$ are 5- or 6-membered monocyclic or bicyclic imides; and

A is a linker of empirical formula $C_{0-12}H_{0-8}F_{0-8}N_{0-2}O_{0-2}$ joining rings $G^{2a}$ and $G^{2b}$. In the graphic depictions of the $G^2$ and $G^3$ groups, the imide (accounting for two carbons, two oxygens and a nitrogen in the empirical formula $C_{4-20}H_{3-12}N_{1-2}O_{2-5}$) is drawn out in the formula above.

In a second aspect, the invention relates to a polymer comprising a first component as above and a second component consisting of a unit of the formula

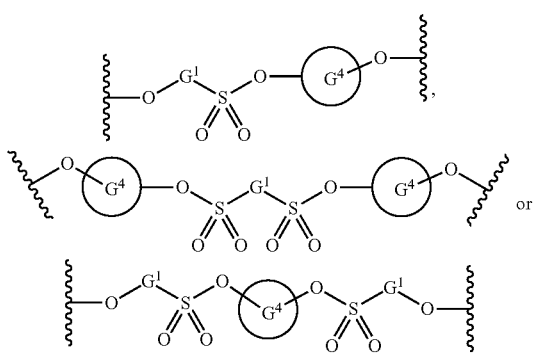

wherein $G^4$ is chosen from phenyl, naphthyl, biphenyl and [-phenyl-R-phenyl-] wherein R is —O—, —S—, —SO—, $SO_2$—, or —$(C_{1-4}H_{2-8})$—.

In a third aspect, the invention relates to monomers useful for preparing the polymers described above. The monomers have the formulae

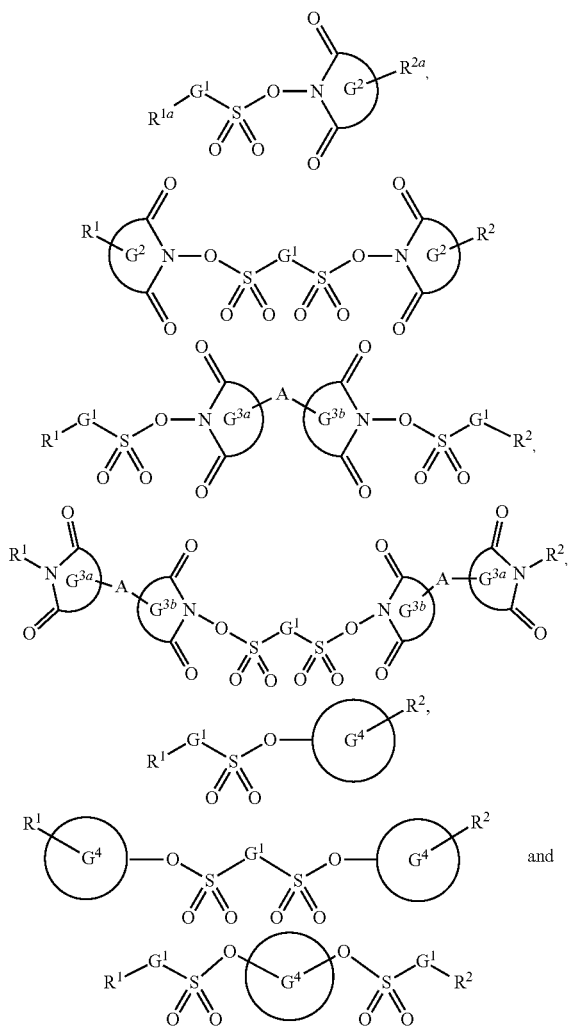

wherein $R^1$ and $R^2$ are chosen independently from —OH, —$NH_2$, —Cl, —Br, —$SO_2Cl$, —N=C=O and —COCl;

$R^{1a}$ is chosen from —OH, —$NH_2$, —Cl, —Br, —N=C=O and —COCl; and $R^{2a}$ is chosen from —$NH_2$, —Cl, —Br, —$SO_2Cl$, —N=C=O and —COCl.

In a further aspect, the invention relates to a method for patterning a substrate comprising:
(a) depositing a polymer as described above on a surface of a substrate;
(b) imagewise exposing the polymer on the surface to actinic radiation; and
(c) developing the exposed polymer to remove portions of the polymer.

In a further aspect, the invention relates to a method for making a semiconductor device comprising:
(a) depositing a polymer as described above on a surface of a substrate;
(b) imagewise exposing the polymer on the surface to actinic radiation;
(c) developing the exposed polymer to remove portions of the polymer and expose portions of the surface;
(d) altering the surface of the substrate; and
(e) removing remaining polymer from the surface.

In a further aspect, the invention relates to a semiconductor device produced by the foregoing method.

In further aspects, the invention relates to a photoresist formulation comprising a solvent and a polymer as described above and to a photoresist comprising a polymer as described above.

DETAILED DESCRIPTION OF THE INVENTION

In one aspect, the invention disclosed herein relates to a polymer comprising at least a first component and a second component. The first component is photolytically stable and acid-stable. The second component is chosen from units of the formulae

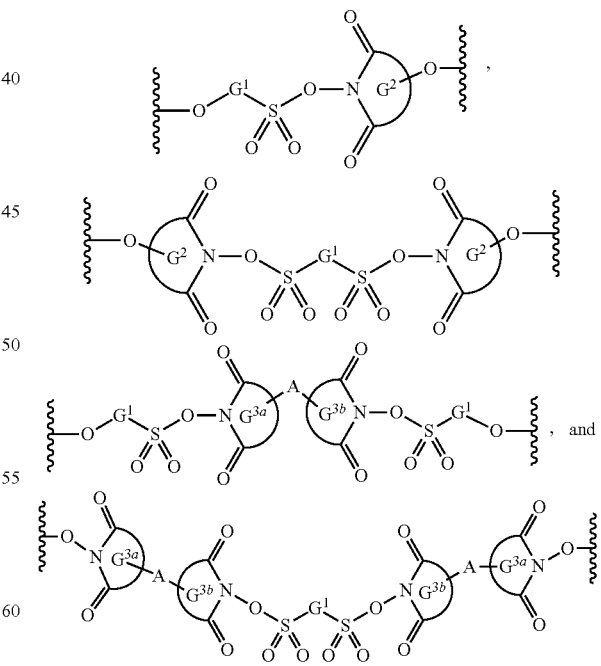

The polymer may contain mixtures of various monomers/repeating units described herein. It may also contain other monomers/repeating units in addition to those described herein. Indeed, the polymer may comprise predominantly other repeating units. As long as a polymer contains a residue corresponding to the "first component" and the "second component" described herein, the polymer is to be considered within the scope of the invention. Preferably each polymer chain contains at least two recurrences of each first and second component. As a practical consideration, the polymer will usually contain a sufficient plurality of the second component to allow for fragmentation of the polymer in a convenient time frame to be useful for photolithography. In most embodiments, the polymers have molecular weights of 6,000 g/mol or greater, and they contain 10 or more residues of the second component.

In some embodiments, $G^1$ is selected from phenyl, $(C_2\text{-}C_6)$ alkyl, fluorophenyl, fluoro$(C_2\text{-}C_6)$alkyl, benzyl, biphenyl and diphenyl ether. Examples of $G^1$ include:

In some embodiments, $G^2$ is chosen from

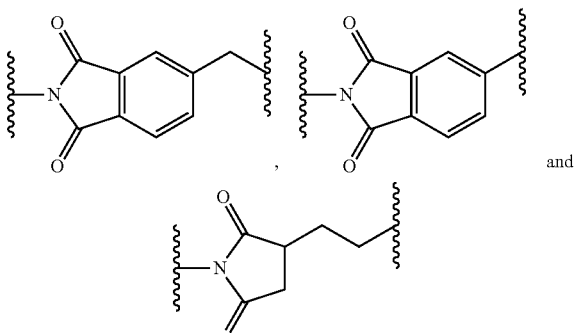

In some embodiments, $G^{3a}$ and $G^{3b}$ are chosen from wherein "a" indicates the point of attachment to A.

In some embodiments, the $G^{3a}$-A-$G^{3b}$ combination is chosen from

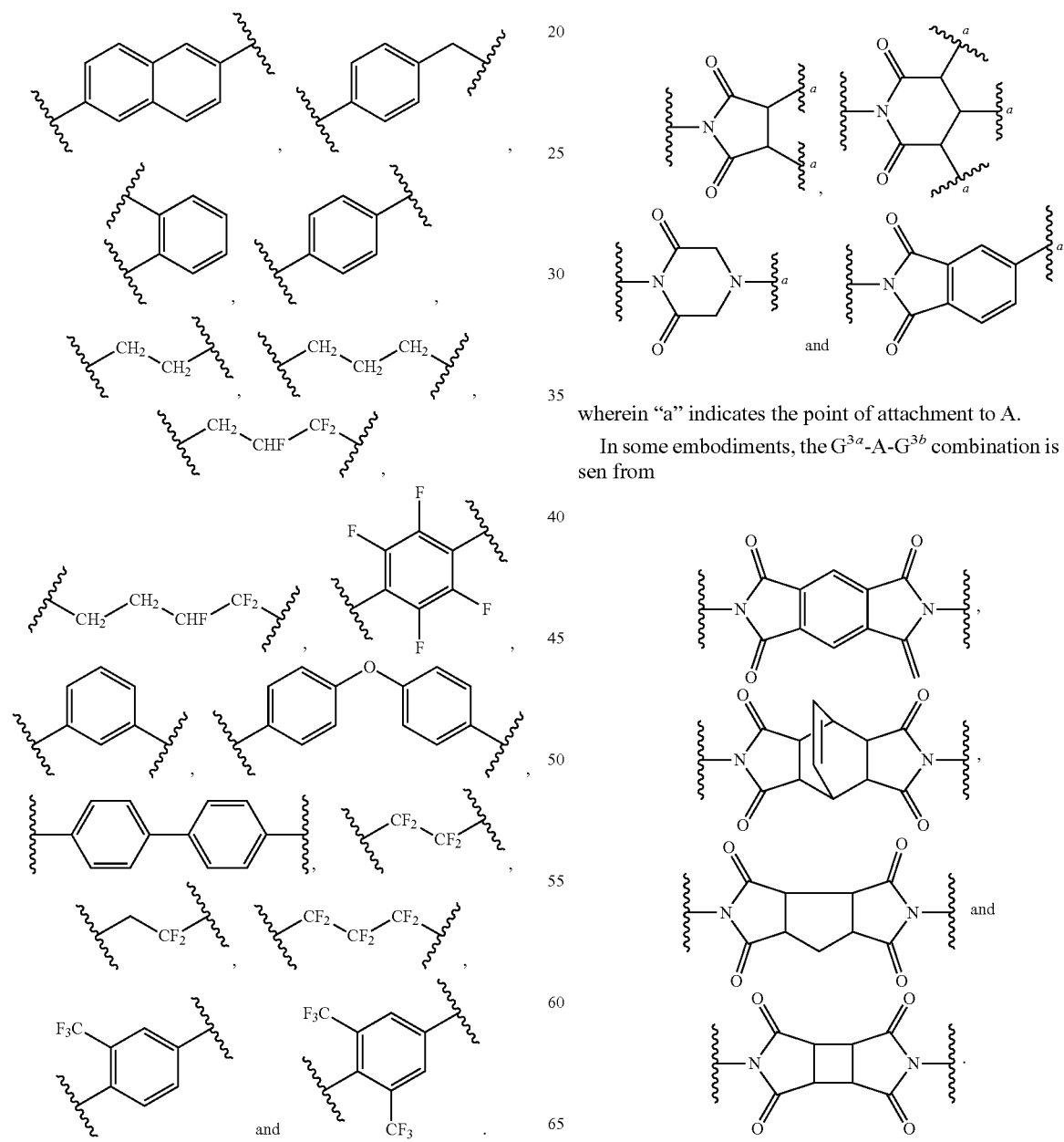

In other embodiments, the $G^{3a}$-A-$G^{3b}$ combination is chosen from

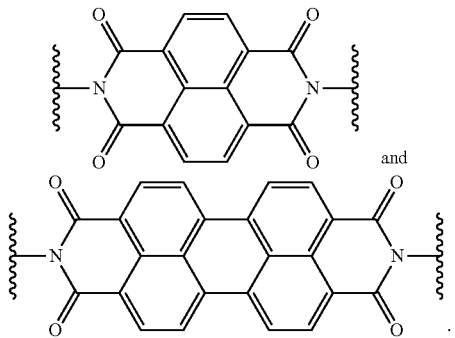

and

In other embodiments, $G^{3a}$ and $G^{3b}$ are chosen from

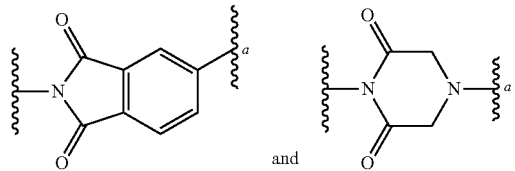 [SMILES: *c1ccc2c(c1)C(=O)N(*)C2=O ; *N1CC(=O)N(*)C(=O)C1]

and A is chosen from

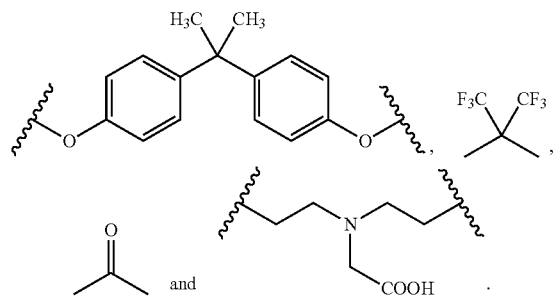

In all of the foregoing embodiments, the imide is embedded in a five or six-membered ring, i.e. the imide is found in the form of a dioxopyrrolidine or dioxopiperidine.

Other possible photolabile residues, $G^6$, that could be substituted for $G^2$ and $G^3$ include

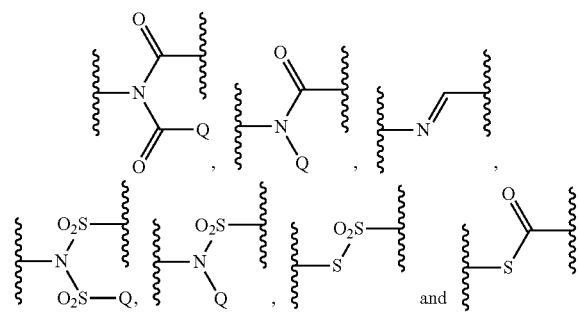

in which Q is an alkyl, aryl, fluoroalkyl or fluoroaryl residue.

In some embodiments second component consists of a unit of the formula

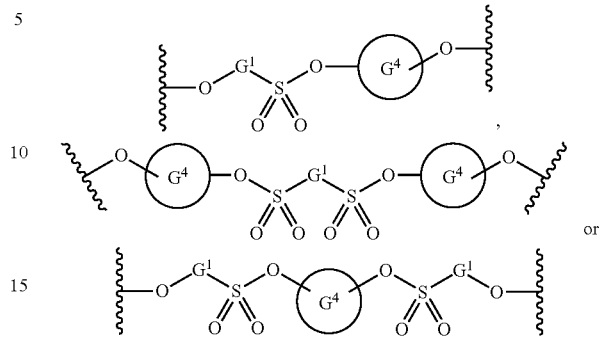

in which $G^4$ is chosen from phenyl, naphthyl, biphenyl and [-phenyl-R-phenyl-] wherein R is —O—, —S—, —SO—, SO$_2$—, or —(C$_{1-4}$H$_{2-8}$)—. In some embodiments $G^1$ is selected from phenyl, (C$_2$-C$_6$)alkyl, fluorophenyl, fluoro(C$_2$-C$_6$)alkyl, benzyl, biphenyl and diphenyl ether.

In some embodiments $G^4$ is chosen from

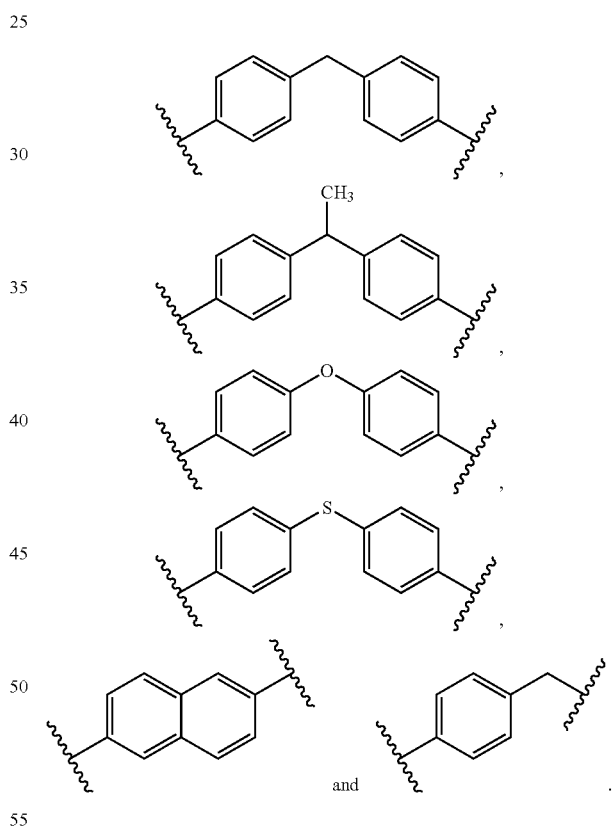

The polymer described above may be a polyester in which the first component is of formula —CO-$G^5$-CO— wherein $G^5$ is selected from an alkane, a fluoroalkane, an arene, a fluoroarene, a diaryl ether and a diaryl. The polymer described above may also be a polyether in which the first component is of formula -$G^5$- wherein $G^5$ is selected from an alkane, a fluoroalkane, an arene, a fluoroarene, a diaryl ether and a diaryl. The polymer described above may also be a polyurethane in which the first component is of formula —C(=O)NH-$G^5$-NHC(=O)— wherein $G^5$ is selected from an alkane, a fluoroalkane, an arene, a fluoroarene, a diaryl ether and a diaryl.

The polymer described above may also be a polyester, polyether or polyurethane that comprises a third, acid-labile, component. The third component may be of formula —CO-G$^6$-CO— or —O-G$^6$-O—, wherein G$^6$ contains a tertiary ether or tertiary ester function.

The polymers of the invention may be constructed from monomers of the formula

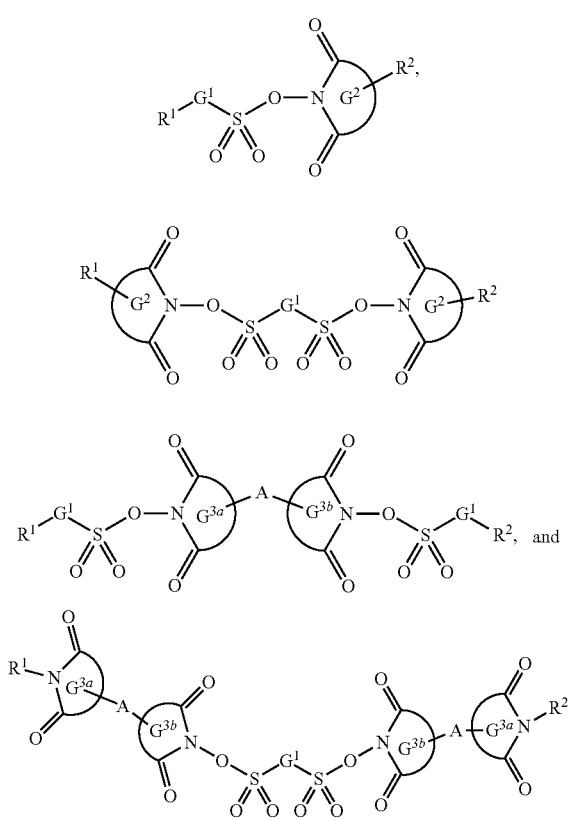

Although R$^1$ and R$^2$ may be chosen independently from —OH, —NH$_2$, —Cl, —Br, —SO$_2$Cl, —N=C=O and —COCl, R$^1$ and R$^2$ will usually be the same due to the practical consideration of the cost of syntheses. To construct a polyester, R$^1$ and R$^2$ may be either —OH or —COCl. To construct a polyether, R$^1$ and R$^2$ may be either —OH or halogen, preferably —Br or —Cl. To construct a polyurethane, R$^1$ and R$^2$ may be either —OH or —N=C=O. Examples of monomers useful in constructing polymers of the invention include those in which R$^1$ and R$^2$ are both —OH:

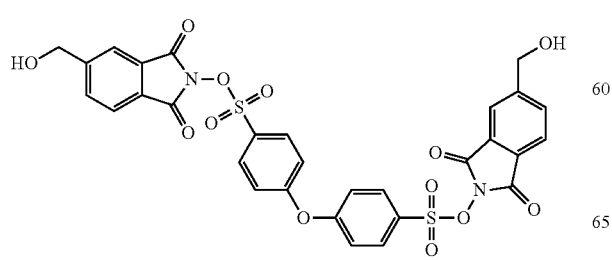

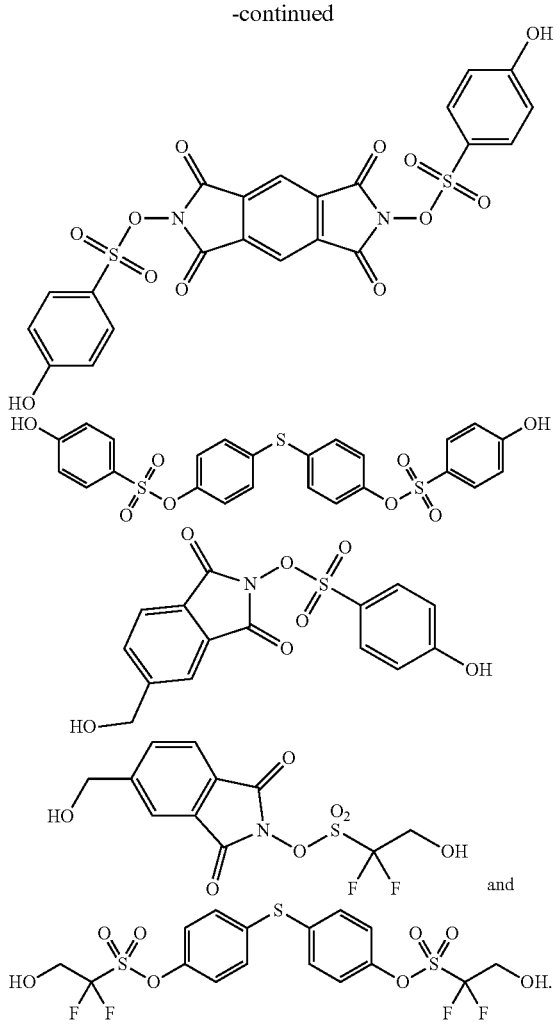

To construct polyesters these monomers can be reacted with such diacyl chlorides as

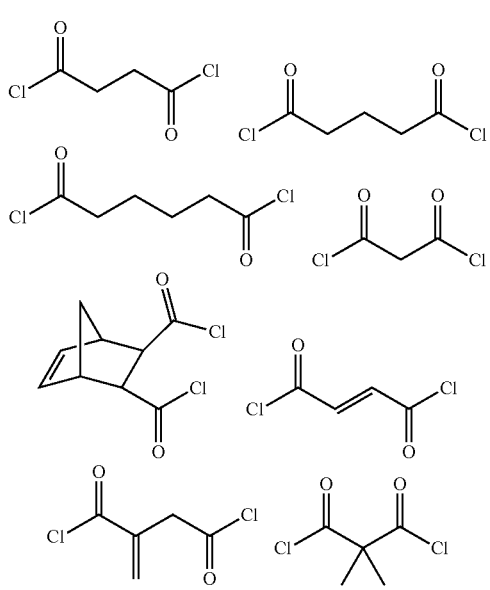

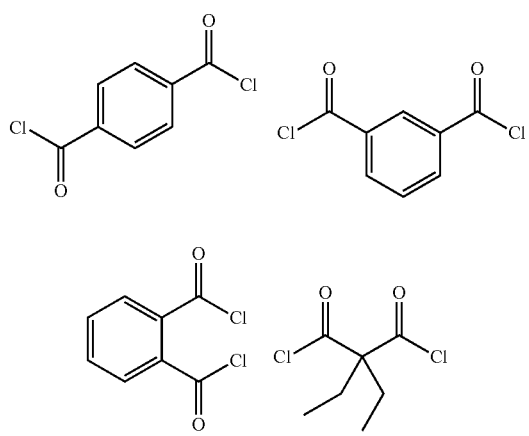
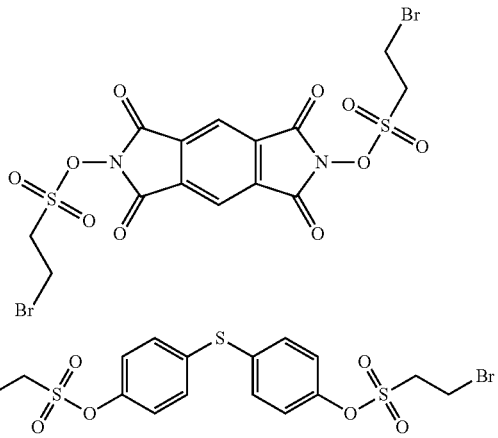
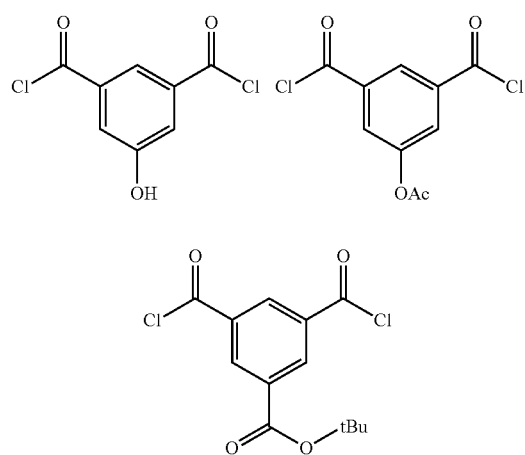
In one embodiment, the monomer is of formula
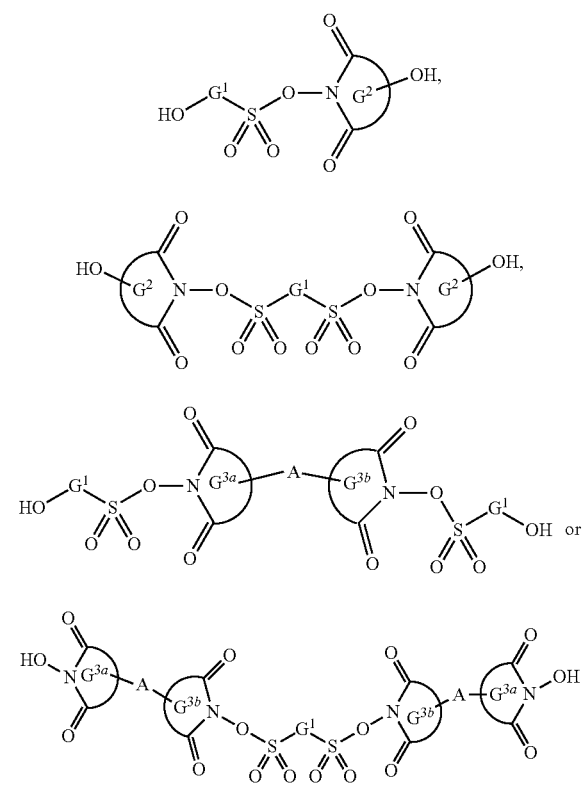
Other examples of monomers useful in constructing polymers of the invention include those in which $R^1$ and $R^2$ are both —Br:
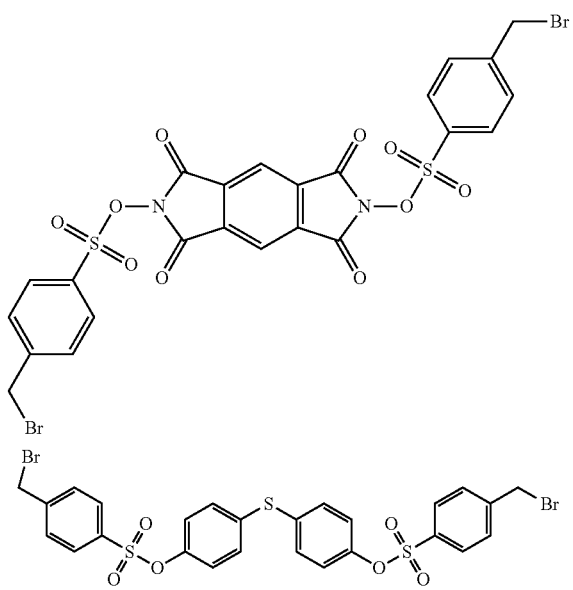
Examples of monomers of the formulae
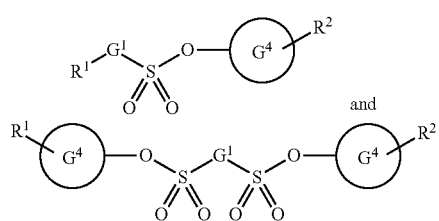
and are monomers of the formula

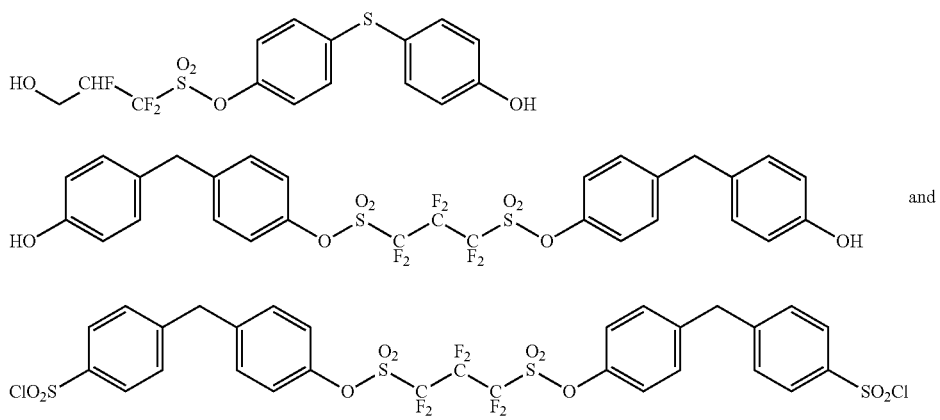

An example of a monomer of the formula

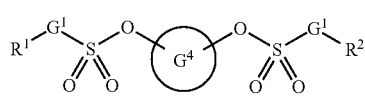

is a monomer of the formula

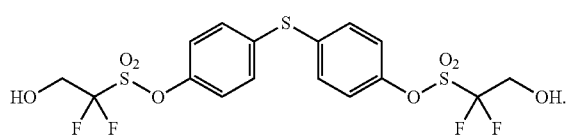 [SMILES: O=S(=O)(Oc1ccc(Sc2ccc(OS(=O)(=O)C(F)(F)CO)cc2)cc1)C(F)(F)CO]

Embodiments of the monomers parallel the embodiments of the polymers in the representative values of the various G groups.

Throughout this specification the terms and substituents retain their definitions.

Alkyl is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ Hydrocarbon includes alkyl, cycloalkyl, polycycloalkyl, alkenyl, alkynyl, aryl and combinations thereof. Examples include benzyl, phenethyl, cyclohexylmethyl, camphoryl and naphthylethyl. The term "carbocycle" is intended to include ring systems consisting entirely of carbon but of any oxidation state. Thus ($C_3$-$C_{10}$) carbocycle refers to such systems as cyclopropane, benzene and cyclohexene; ($C_8$-$C_{12}$) carbopolycycle refers to such systems as norbornane, decalin, indane and naphthalene.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons. Methoxy is preferred. For the purpose of this application, alkoxy and lower alkoxy include methylenedioxy and ethylenedioxy.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, heterocyclyl etc. refer to alkyl, aryl, or heterocyclyl wherein one or more H atoms in each residue are replaced with halogen, haloalkyl, alkyl, hydroxyl, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, aryl, benzyl, heteroaryl, phenoxy, benzyloxy, or heteroaryloxy.

The term "halogen" means fluorine, chlorine, bromine or iodine.

The term "component" means a repeating unit, covalently bonded in a polymer. By repeating is meant that the residue occurs at least two times in the polymer. The component can be in the polymer backbone, a side-chain or a cross-link. Preferably, the component is a repeating unit in the polymer backbone. The terms "repeating unit" and "structural unit" are terms of art [see M. P. Stevens, *Polymer Chemistry*, Third Edition, Oxford University Press (1999)] and may be used interchangeably with "component".

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups".

In the case of the present invention, the functionalities that must be protected include carboxylic acids and alcohols and occasionally amines. Suitable groups for that purpose are discussed in standard textbooks in the field of chemistry, such as *Protective Groups in Organic Synthesis* by T. W. Greene and P. G. M. Wuts [John Wiley & Sons, New York, 1999], which is incorporated herein by reference.

Polymers can be synthesized using numerous combinations of commercially available diacid chlorides and diols. Some of the diacid chlorides that can be obtained commercially are outlined in Table 2.

TABLE 2

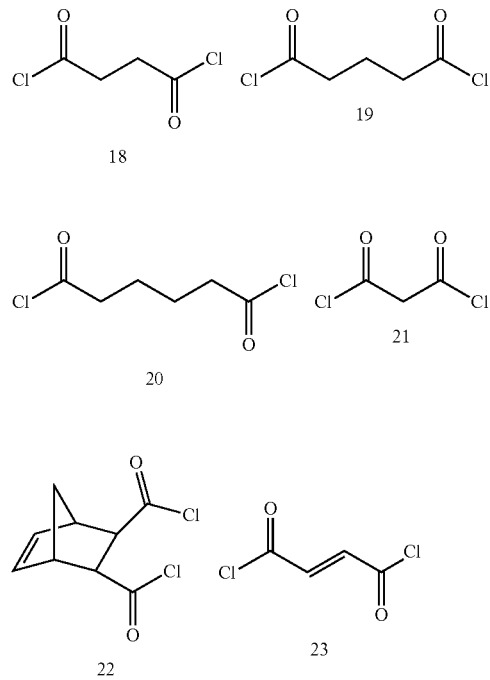

TABLE 2-continued

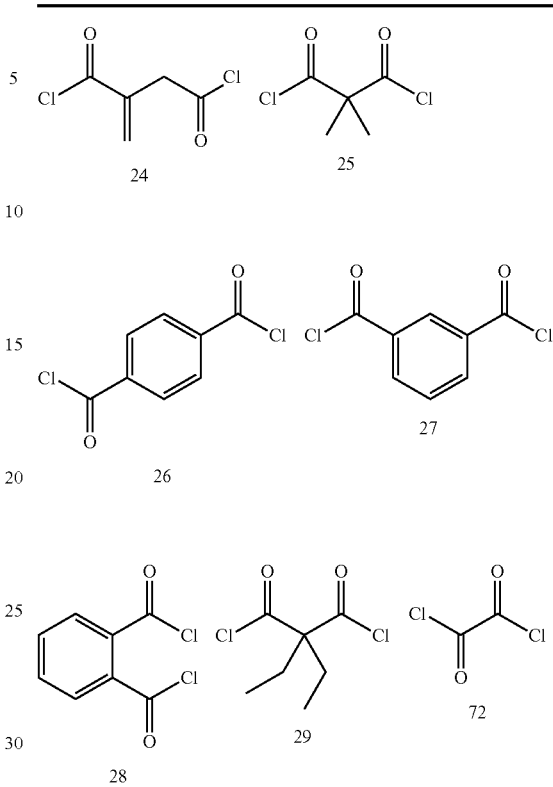

Step-growth polymers are well known and are of great commercial importance. Nylon and PET are high volume examples. Novolak polymers used in I-line resists are also step-growth polymers. Since I-line, however, nearly all of the polymers used in photoresists have been free-radical chain-growth polymers such as those used in the preparation of DUV, 193 nm and EUV photoresists. One of the advantageous characteristics of step-growth polymerization is that the high molecular weight polymers are not created until the end of the polymerization reaction. Since many of the features of polymers for photolithography depend upon the reduction of molecular weight upon photolysis, it is advantageous to prepare polymers with molecular weights of 6,000 g/mol or greater.

Many commercially successful step-growth polyesters are prepared directly from dicarboxylic acids and diols at high temperatures. In the case of some polymers, however, it is preferred to conduct polymerizations at temperatures less than about 40° C. to minimize thermal decomposition. Reacting diacid chlorides with diols is typically considered "overkill" for high volume polyester production, however, for synthesis with tertiary alcohols, moderate temperatures are desirable. To accomplish this, one may convert the tertiary diols to tertiary dialkoxides by reaction with n-BuLi prior to reaction with the diacid chlorides (Scheme 3). These reactions are quite exothermic so that they need to be conducted at controlled temperature to give high yields. An additional feature of this approach is that the by-product of this reaction (LiCl) is easier to remove than pyridine or triethylamine.

Scheme 3

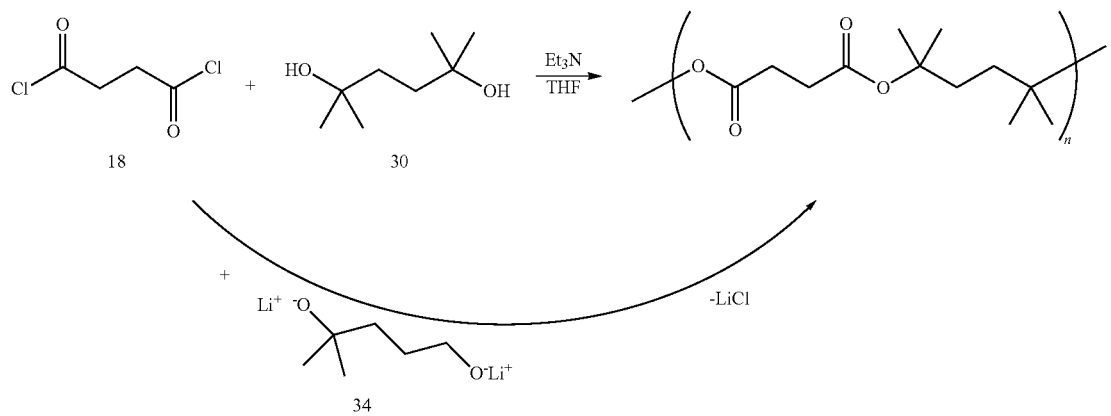

One approach for linking low molecular weight oligomers together at the end of the polymerization is to add unhindered diols, diphenols or diamines such as molecules 35-44 in Table 4. Although these linkages are inactive toward acidolysis, they provide an additional method for building molecular weight since they are more reactive than the tertiary diols toward acid chlorides. Unhindered trifunctional monomers can also be added at the end of the reaction to build molecular weight. In particular, molecules 45-47 can be used to link oligomers together. Trifunctional monomers are also interesting because they can react twice and leave desirable unreacted functional groups such as phenols (adhesion) or amines (quencher base). Similarly, trifunctional monomers such as 30, 31 and 32, having a protected phenol or a tertiary ester capable of deprotection (shown below) could be used. Compounds 48-50 have tertiary amines that will not react with acid chlorides, so will add quencher base to the polymer. With both acids and bases covalently attached to polymers, image blur due to diffusion will be at minimum.

Trace amounts of water present during the polymerization could limit molecular weight by converting acid chlorides to the much less reactive carboxylic acids. To counteract this problem, one can use activating agents 51-53 shown in Table 5. These compounds could be used to couple carboxylic acids and alcohols together to form esters.

TABLE 4

Difunctional Molecules for Mw Build:

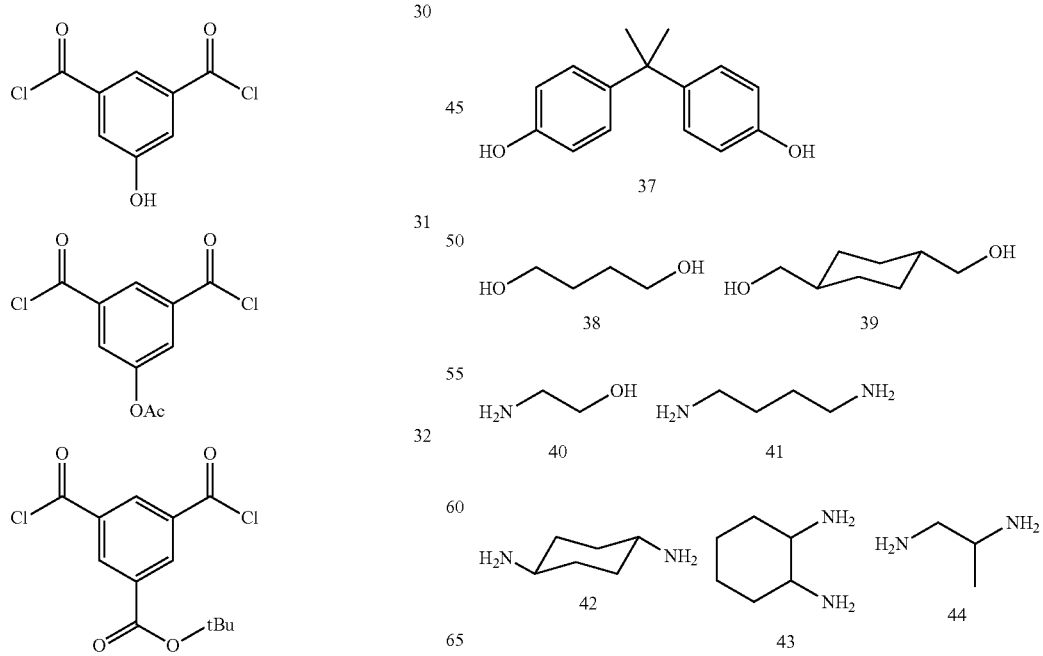

TABLE 4-continued

Trifunctional Molecules for Mw Build:

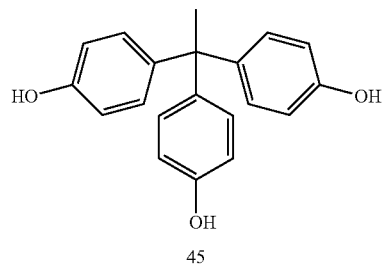 [SMILES: CC(c1ccc(O)cc1)(c1ccc(O)cc1)c1ccc(O)cc1]

45

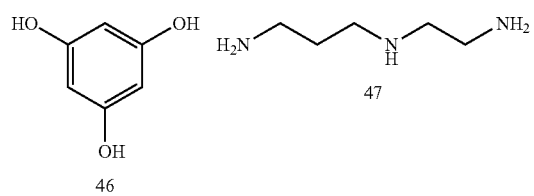 [SMILES: Oc1cc(O)cc(O)c1 ; NCCCNCCN]

Two reactive sites, that will leave base functionality in polymer chain.

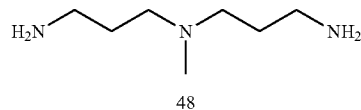

48

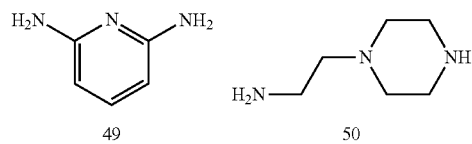 [SMILES: Nc1cccc(N)n1 ; NCCN1CCNCC1]

49   50

TABLE 5

Activating Agents

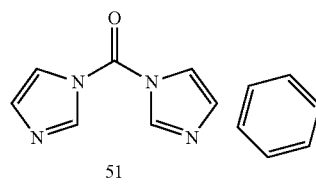

51
1,1-Carbonyldiimidazole

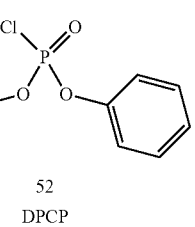

52
DPCP

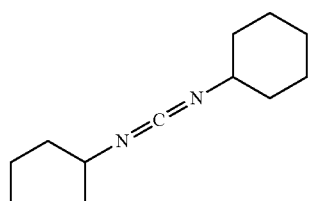

53
DCC

Example 1

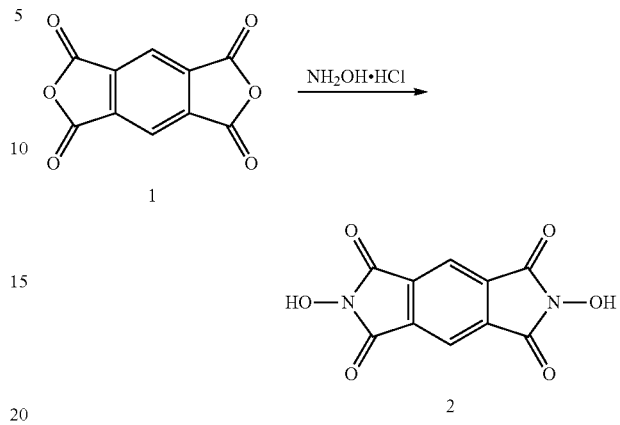

N,N'-Dihydroxypyromellitimide, NDHPI (2): Hydroxylamine hydrochloride (3.18 g, 45.8 mmol) was added to pyridine (25 mL) and stirred at room temperature for 10 mins. A clear solution formed, after which pyromellitic anhydride (1) (5.00 g, 22.9 mmol) was added and the solution was refluxed for overnight at 100° C. To the solid precipitate formed, Conc. HCl (10 mL) was added and the solid was filtered and washed with Cold water. The solid was dried under vacuum. $^1$H NMR (DMSO-$d_6$, 400 MHz): 8.15 (2H, s), 11.25 (2H, s)

Example 2

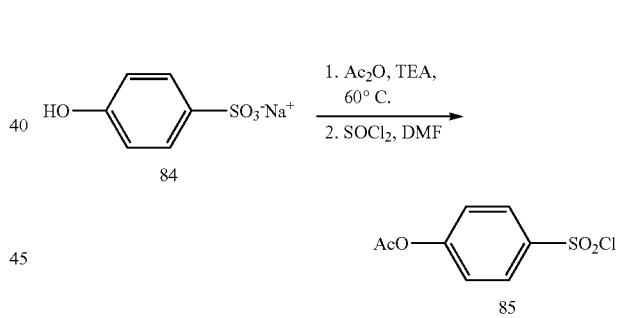

4-Acetoxybenzenesulfonyl chloride (85) was made from the p-phenol sodium sulfonate (84) using established procedures: "Preparation of N-(1,3,4-thiadiazol-2-yl)benzene sulfonamides as PPAR alpha, delta and gamma agonist." Keil, Stefanie; Schoenafinger, Karl; Matter, Hans; Urmann, Matthias; Glien, Maike; Wendler, Wolfgang; Schaefer, Hans-Ludwig; Falk, Eugen. (Sanofi-Aventis Deutschland GmbH, Germany). PCT Int. Appl. (2007), 92 pp. WO 2007039171

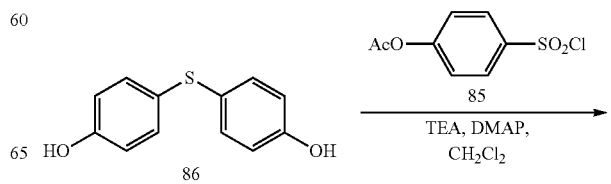

Example 3

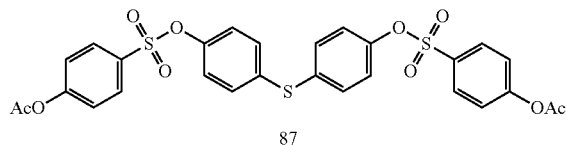
87

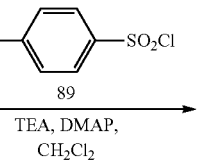
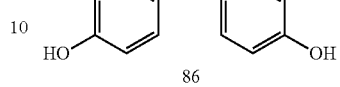
86 + 89 →
TEA, DMAP, CH₂Cl₂

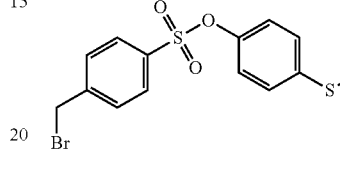
90

4,4'-Thiobis(4,1-phenylene) bis(4-acetoxybenzenesulfonate) (87): A mixture of 4,4'-thiodiphenol (86) (0.100 g, 0.458 mmol) and 4-acetoxybenzene sulfonyl chloride (85) (0.322 g, 1.374 mmol) were dissolved in methylene chloride (5 mL), to which dry triethylamine (0.116 g, 1.145 mmol) and a catalytic amount of 4-dimethylaminopyridine were added and stirred at room temperature for overnight. The reaction mixture was poured into the cold HCl (25 mL, 2 N), and extracted with ethyl acetate. The organic phase was washed with HCl (2×25 mL, 2 N), brine (1×25 mL), dried over Na₂SO₄, and evaporated to dryness. (0.199 g, 71% yield). $^1$H NMR (400 MHz, CDCl₃) δ 8.02 (d, 4H, Ar—H), 7.52 (d, 4H, Ar—H), 7.38 (d, 4H, Ar—H), 7.16 (d, 4H, Ar—H), 2.40 (s, 6H, CH₃).

4,4'-Thiobis(4,1-phenylene) bis(4-(bromomethyl)benzenesulfonate) (90): A mixture of 4,4'-thiodiphenol (86) (1.00 g, 4.6 mmol) and triethylamine (1.16 g, 11.45 mmol) were dissolved in methylene chloride (20 mL) and 4-(bromomethyl)benzene sulfonyl chloride (89) (3.087 g, 11.45 mmol) and a catalytic amount of 4-dimethylaminopyridine were added. The reaction mixture was stirred at room temperature overnight, poured into the cold HCl (25 mL, 2 N), and extracted with ethyl acetate. The organic phase was washed with HCl (2×25 mL, 2 N), brine (1×25 mL), dried over Na₂SO₄, and evaporated to dryness. (2.1 g, 67% yield). $^1$H NMR (400 MHz, CDCl₃) δ 7.90 (d, 4H, Ar—H), 7.76 (d, 4H, Ar—H), 7.31 (d, 4H, Ar—H), 7.08 (d, 4H, Ar—H), 4.84 (s, 4H, CH₂).

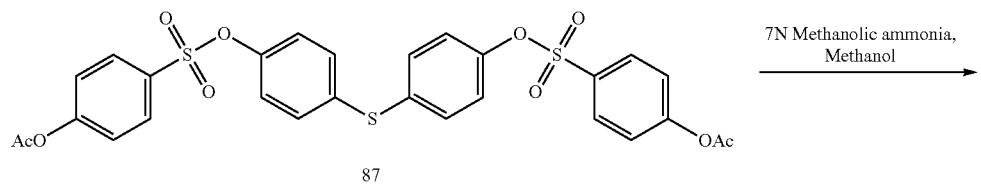
87
→ 7N Methanolic ammonia, Methanol

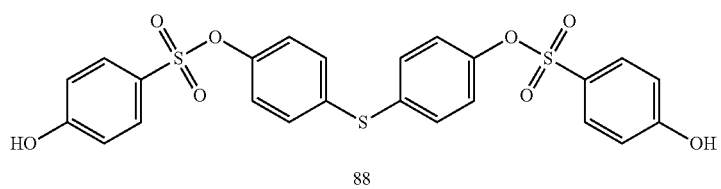
88

4,4'-Thiobis(4,1-phenylene) bis(4-hydroxybenzenesulfonate) (88): A mixture of 4,4'-thiobis(4,1-phenylene) bis(4-acetoxybenzenesulfonate) (87) (0.2 g, 0.3 mmol) is stirred in 7N methanolic ammonia for 1 hr at room temperature. Methanol was removed under reduced pressure and the residue was taken into EtOAc (50 mL). The organic layer was washed with 1N HCl (2×25 mL), water (2×25 mL) and brine (1×25 mL) and dried over Na₂SO₄ and evaporated to dryness. (0.07 g, 45% yield). $^1$H NMR (400 MHz, CDCl₃) δ 7.69 (d, 4H, Ar—H), 7.29 (d, 4H, Ar—H), 7.03 (d, 8H, Ar—H).

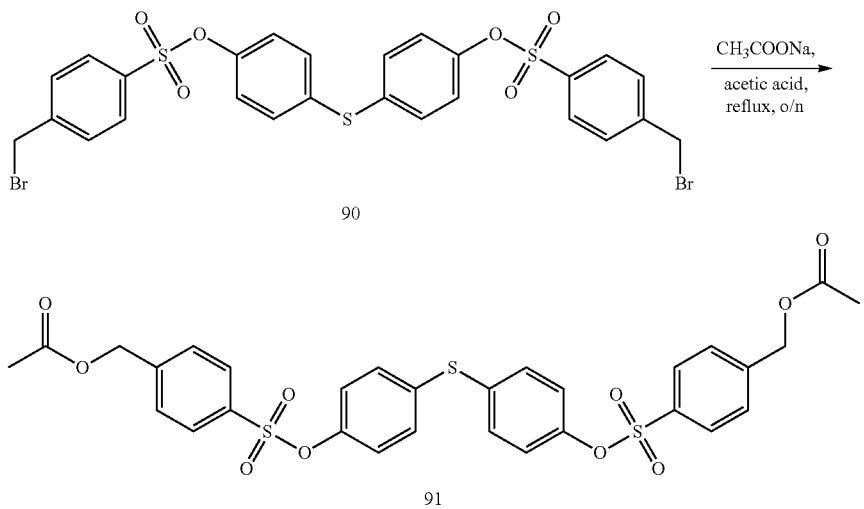

4,4'-Thiobis(4,1-phenylene) bis(4-(acetoxymethyl)benzenesulfonate) (91): A mixture of 4,4'-thiobis(4,1-phenylene) bis(4-(bromomethyl)benzenesulfonate) (90) (0.2 g, 0.3 mmol) and sodium acetate (0.06 g, 0.73 mmol) was dissolved in acetic acid (3 mL) and refluxed for 24 hr. The reaction mixture was dissolved in ethyl acetate and the organic layer was washed with aq. NaHCO$_3$ (4×25 mL), water (3×25 mL) and brine (1×25 mL) and dried (Na$_2$SO$_4$) and evaporated under reduced pressure. (0.146 g, 78% yield). $^1$H NMR (400 MHz, CDCl$_3$) δ 7.88 (d, 4H, Ar—H), 7.66 (d, 4H, Ar—H), 7.32 (d, 4H, Ar—H), 7.08 (d, 4H, Ar—H), 5.24 (s, 4H, CH$_2$), 2.09 (s, 6H, CH$_3$).

4,4'-Thiobis(4,1-phenylene) bis(4-(hydroxymethyl)benzenesulfonate) (92): A mixture of 4,4'-thiobis(4,1-phenylene) bis(4-(acetoxymethyl)benzenesulfonate) (91) (0.146 g, 0.227 mmol) and 7N methanolic ammonia (0.227 mL) was dissolved in methanol and stirred for 1 hr at room temperature. Methanol was removed under reduced pressure and the residue was taken into EtOAc (50 mL). The organic layer was washed with 1N HCl (2×25 mL), water (2×25 mL) and brine (1×25 mL) and dried over Na$_2$SO$_4$ and evaporated to dryness. (0.076 g, 56% yield). $^1$H NMR (400 MHz, CDCl$_3$) δ 7.82 (d, 4H, Ar—H), 7.64 (d, 4H, Ar—H), 7.29 (d, 4H, Ar—H), 7.05 (d, 4H, Ar—H), 4.78 (s, 4H, CH$_2$), 4.48 (br.s, 2H, OH).

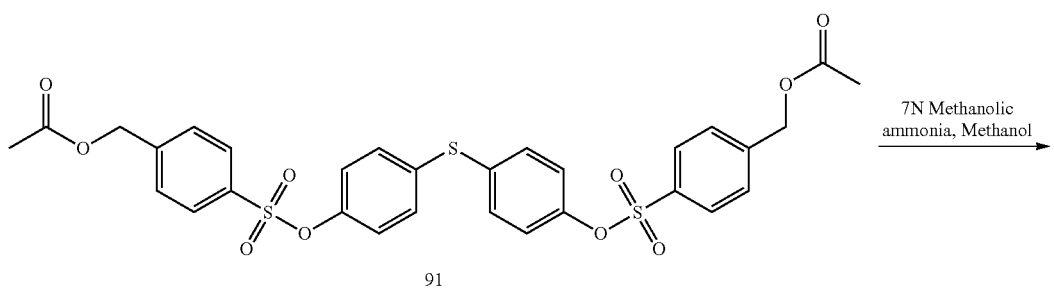

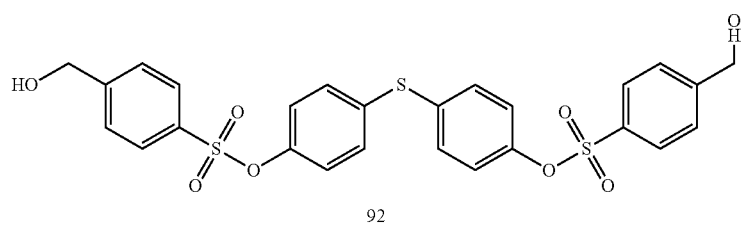

Example 4

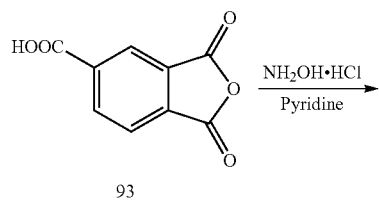

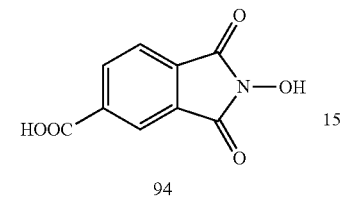

N-Hydroxyphthalimide-4-carboxylic acid (94) was made from commercially available trimellitic anhydride (93) using a procedure analogous to example (1) and established procedure: "Alkane Oxidation with Air Catalyzed by Lipophilic N-Hydroxyphthalimides without Any Solvent." Sawatari, Naoko; Yokota, Takahiro; Sakaguchi, Satoshi; Ishii, Yasutaka. Journal of Organic Chemistry (2001), 66(23), 7889-7891.

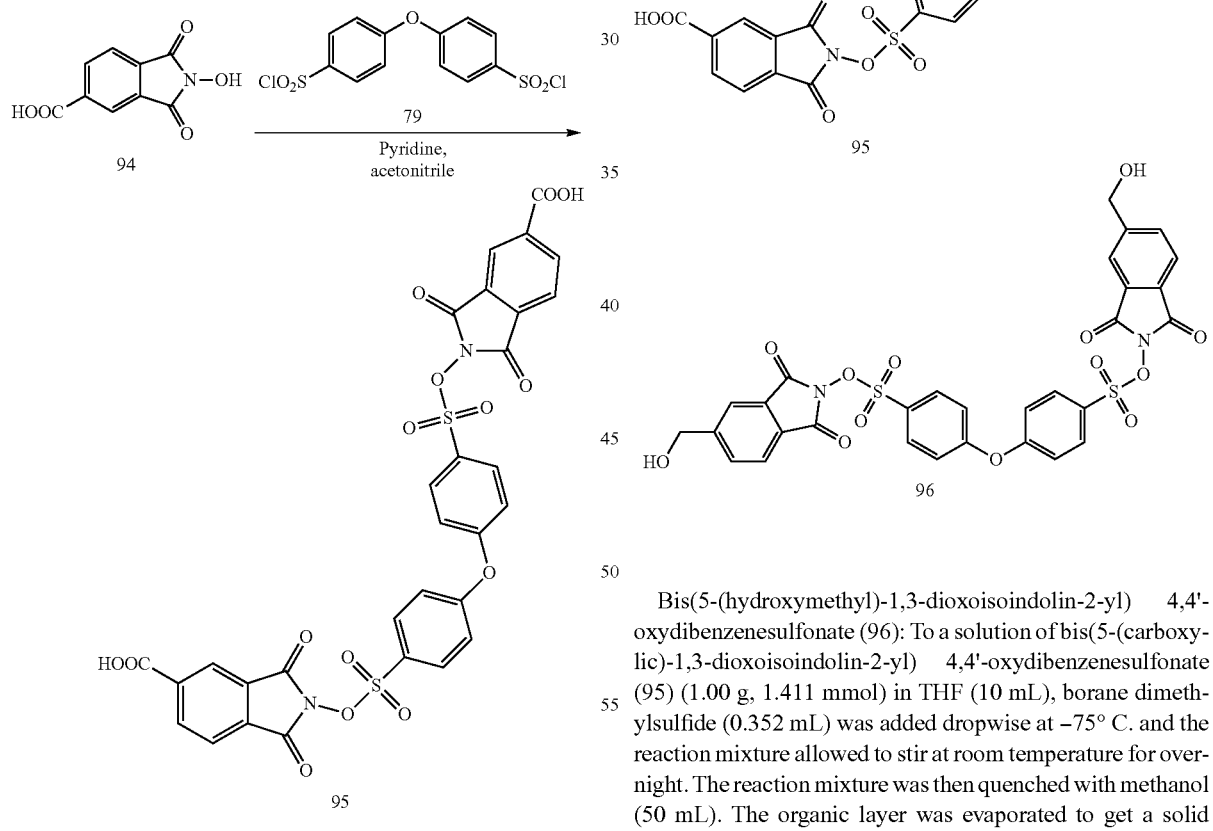

Bis(5-(carboxylic)-1,3-dioxoisoindolin-2-yl) 4,4'-oxydibenzenesulfonate (95): A mixture of N-Hydroxyphthalimide-4-carboxylic acid (94) (1.128 g, 5.446 mmol) and 4,4'-oxybis(benzenesulfonyl chloride) (79) (1.00 g, 2.723 mmol) were dissolved in acetonitrile (10 mL) in presence of pyridine (1.722 g, 21.78 mmol) and stirred for overnight at room temperature, poured into the cold HCl (25 mL, 2 N), and extracted with ethyl acetate. The organic phase was washed with HCl (2×25 mL, 2 N), brine (1×25 mL), dried over $Na_2SO_4$, and evaporated to dryness. (1.852 g, 48% yield). $^1$H NMR (400 MHz, $CDCl_3$) δ 8.57 (d, 2H, Ar—H), 8.43 (s, 2H, Ar—H), 8.26 (d, 4H, Ar—H), 8.11 (d, 2H, Ar—H), 7.52 (d, 4H, Ar—H).

Bis(5-(hydroxymethyl)-1,3-dioxoisoindolin-2-yl) 4,4'-oxydibenzenesulfonate (96): To a solution of bis(5-(carboxylic)-1,3-dioxoisoindolin-2-yl) 4,4'-oxydibenzenesulfonate (95) (1.00 g, 1.411 mmol) in THF (10 mL), borane dimethylsulfide (0.352 mL) was added dropwise at −75° C. and the reaction mixture allowed to stir at room temperature for overnight. The reaction mixture was then quenched with methanol (50 mL). The organic layer was evaporated to get a solid residue which was dissolved in EtOAc. The EtOAc layer was washed with water (3×50 mL), brine (1×25 mL), dried ($Na_2SO_4$) and was evaporated to get a residue purified by column chromatography. (0.124 g, 13% yield). $^1$H NMR (400 MHz, $CDCl_3$) δ 9.18 (d, 2H, Ar—H), 8.73 (s, 2H, Ar—H), 8.52 (d, 4H, Ar—H), 8.19 (d, 2H, Ar—H), 8.02 (d, 4H, Ar—H), 3.82 (s, 4H, $CH_2$).

Example 5

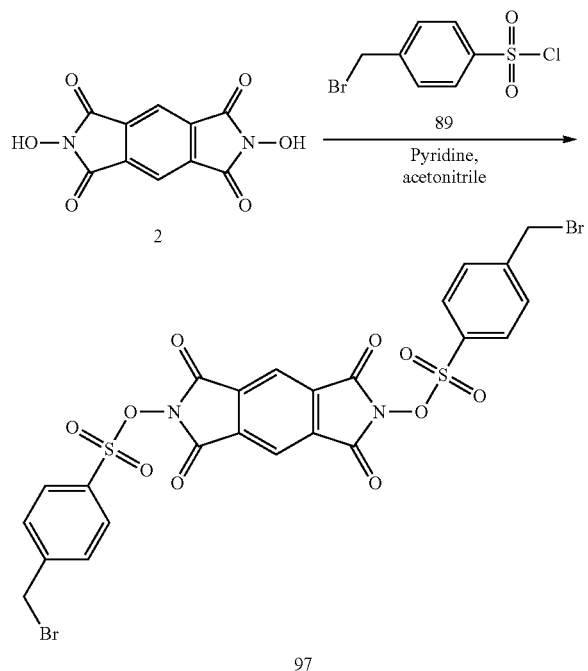

1,3,5,7-Tetraoxopyrrolo[3,4-f]isoindole-2,6(1H,3H,5H, 7H)-diyl-bis(4-(bromomethyl)benzenesulfonate) (97): A mixture of N,N'-Dihydroxypyromellitimide, NDHPI (2) (0.2 g, 0.806 mmol) and (4-bromomethyl)benzene sulfonyl chloride (89) (0.651 g, 2.418 mmol) were dissolved in N,N'-dimethylacetamide (1.755 g, 20.149 mmol) in presence of pyridine (0.121 g, 1.53 mmol) and the reaction mixture was stirred at room temperature for 2 hrs. A solid precipitated out upon adding water (5 mL), which was filtered and dried under vacuum. (0.124 g, 13% yield). $^1$H NMR (400 MHz, CDCl$_3$) δ 8.41 (s, 2H, Ar—H), 8.15 (d, 4H, Ar—H), 7.81 (d, 4H, Ar—H), 4.96 (s, 4H, CH$_2$).

Example 6

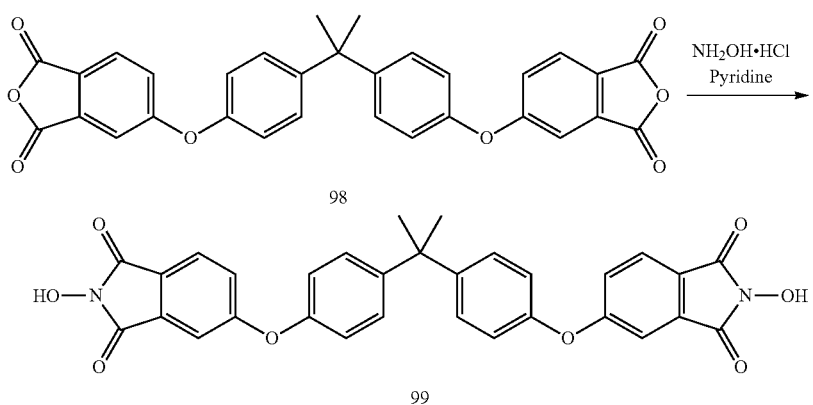

N,N'-Dihydroxy ultemimide (99) was made from commercially available Ultem anhydride (98) using a procedure analogous to Example (1) and established procedure: "N-(allyloxy)imides as reactive monomers." Dao, Buu; Morton, Trevor; Ger. Offen. (1996), DE 19540107.

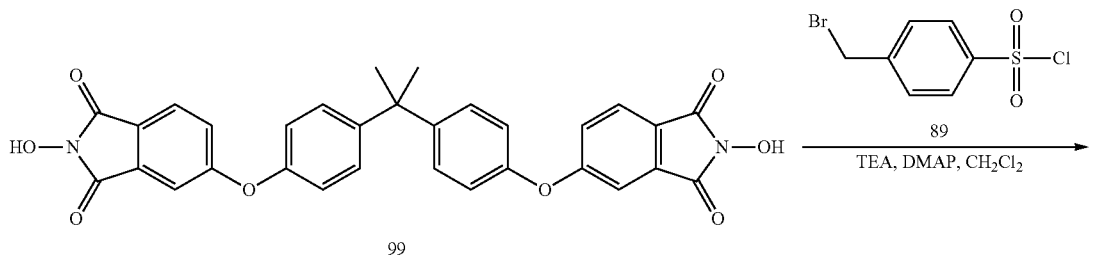

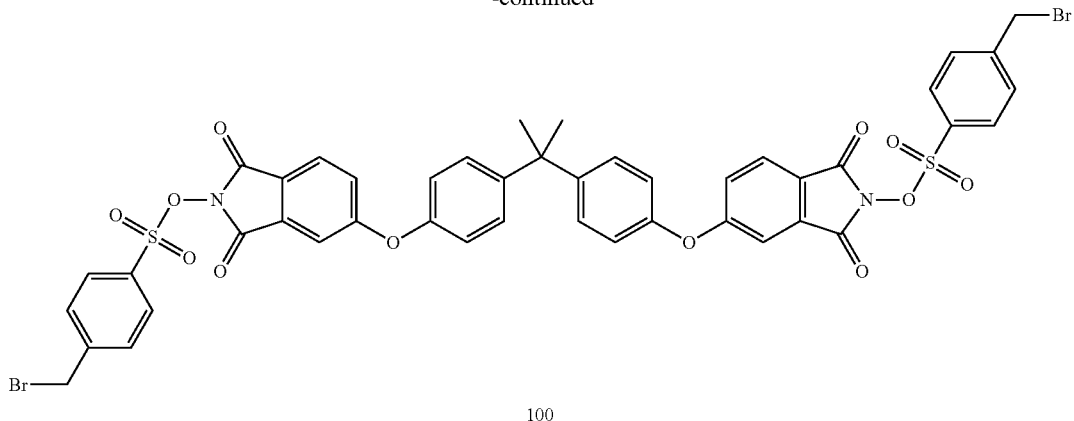

100

5,5'-(4,4'-(Propane-2,2-diyl)bis(4,1-phenylene))bis(oxy)bis(1,3-dioxoisoindoline-5,2-diyl) bis(4-(bromomethyl)benzenesulfonate) (100): A mixture of N,N'-dihydroxy ultemimide (99) (0.2 g, 0.37 mmol) and triethylamine (0.091 g, 0.908 mmol) were dissolved in methylene chloride (10 mL) and 4-(bromomethyl)benzene sulfonyl chloride (89) (0.293 g, 1.089 mmol) and a catalytic amount of 4-dimethylaminopyridine were added and the reaction mixture was stirred at room temperature for overnight, poured into the 1N $NH_4Cl$ (25 mL), and extracted with ethyl acetate. The organic phase was washed with 1N $NH_4Cl$ (5×25 mL), water (3×25 mL), brine (1×25 mL), dried over $Na_2SO_4$, and evaporated to dryness. (0.251 g, 68% yield). $^1H$ NMR (400 MHz, $CDCl_3$) δ 8.03 (m, 4H, Ar—H), 7.78 (d, 2H, Ar—H), 7.61 (d, 4H, Ar—H), 7.30 (m, 6H, Ar—H), 6.99 (d, 4H, Ar—H), 4.64 (s, 4H, $CH_2$), 1.72 (s, 6H. $CH_3$).

Example 7

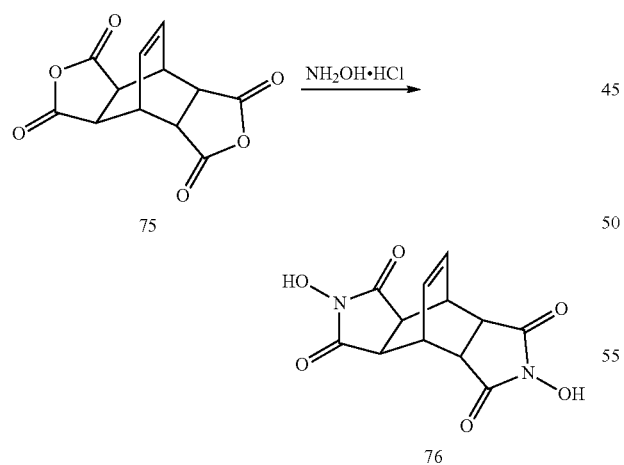

3a,4,4a,7a,8,8a-Hexahydro-2,6-dihydroxy-4,8-ethenobenzo[1,2-c:4,5-c']dipyrrole-1,3,5,7(2H,6H)-tetrone (76): The dihydroxy diimide is made in the following manner. Bicycle[2,2,2]oct-7-ene-2,3,5,6-tetracarboxylic dianhydride (75) is reacted with 2 equivalents of hydroxylamine hydrochloride in anhydrous pyridine[2] at 100° C. for 15 hrs. The reaction mixture is quenched with 6% acetic acid to precipitate the product.

Example 8

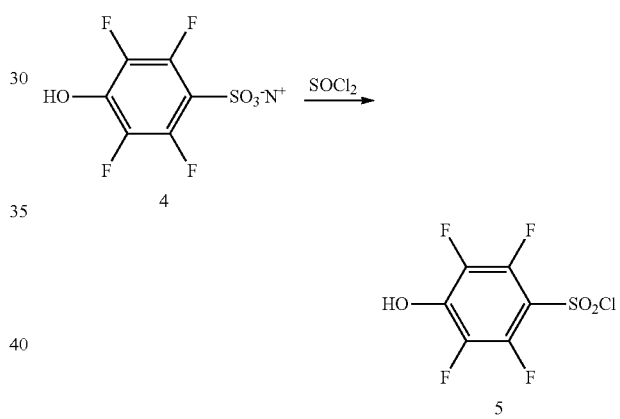

2,3,5,6-Tetrafluoro-4-hydroxybenzene-1-sulfonyl chloride (5): The sulfonyl chloride is prepared in the following manner. The sodium salt of 2,3,5,6-tetrafluoro-4-hydroxybenzenesulfonate [see Kyle et al., Tet. Lett. 40, 1471-1474 (1999)] is converted to its corresponding sulfonyl chloride by reacting with thionyl chloride in catalytic DMF [see Campbell et al. J. Org. Chem. 38, 1047 (1973)].

Example 9

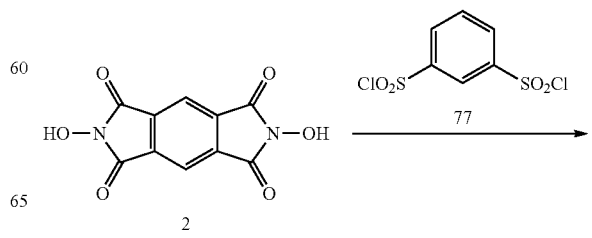

-continued

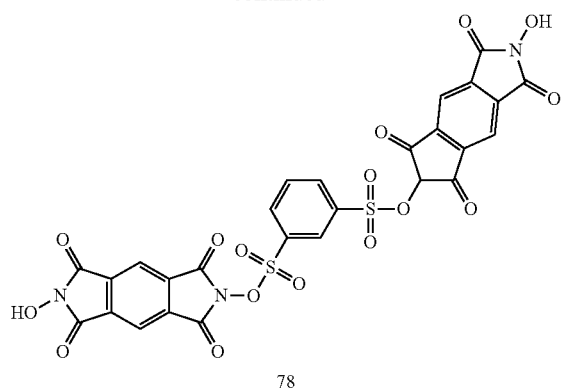

78

Bis(6-hydroxy-1,3,5,7-tetraoxo-6,7-dihydropyrrolo[3,4-f]isoindol-2(1H,3H,5H)-yl)benzene-1,3-disulfonate (78): The PAG-diol is made in the following manner. Two equivalents of N,N'-Dihydroxypyromellitimide (2) is heated with one equivalent of benzene-1,3-disulfonyl dichloride (77) in anhydrous pyridine at 90° C. for 16 hrs. The product, bis(6-hydroxy-1,3,5,7-tetraoxo-6,7-dihydropyrrolo[3,4-f]isoindol-2(1H,3H,5H)-yl)benzene-1,3-disulfonate (78) is obtained upon acidification with 6% acetic acid.[2]

Example 10

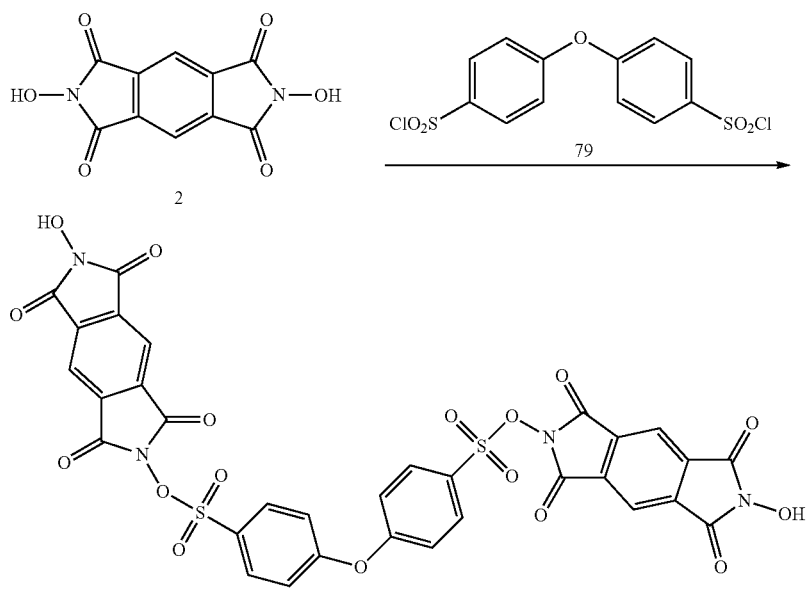

Bis(6-hydroxy-1,3,5,7-tetraoxo-6,7-dihydropyrrolo[3,4-f]isoindol-2(1H,3H,5H)-yl) 4,4'-oxydibenzenesulfonate (80): The PAG-diol is made in the following manner. Two equivalents of N,N'-Dihydroxypyromellitimide (2), is heated with one equivalent of 4,4'-oxybis(benzenesulfonyl chloride) (79) in presence of anhydrous pyridine at 100° C. for 15 hrs. The product, bis(6-hydroxy-1,3,5,7-tetraoxo-6,7-dihydropyrrolo[3,4-f]isoindol-2(1H,3H,5H)-yl) 4,4'-oxydibenzenesulfonate (80) is obtained on acidification with 6% acetic acid.

Example 11

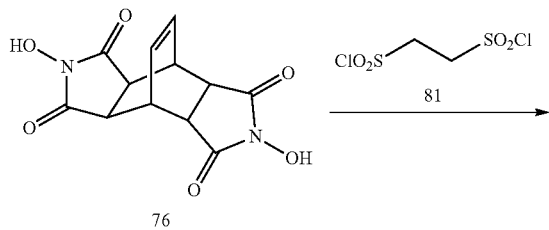

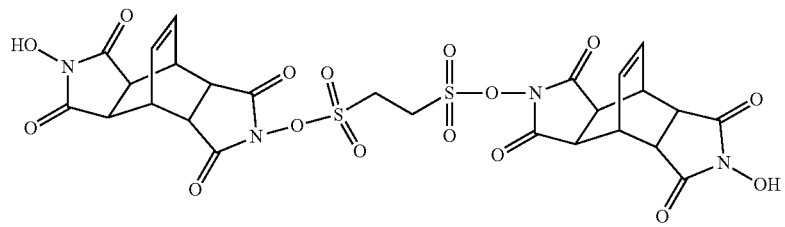

82

1,2-Bis(1,2,4,5-dihydroxyiminebicyclo[2.2.1]heptane)-ethyl sulfonate (82): The PAG-diol is made in the following manner. Two equivalents of N,N'-3a,4,4a,7a,8,8a-hexahydro-2,6-dihydroxy-4,8-ethenobenzo[1,2-c:4,5-c']dipyrrole-1,3,5,7(2H,6H)-tetrone (76), is heated with one equivalent of ethane-1,2-disulfonyl chloride (81) in presence of anhydrous pyridine at 100° C. for 15 hrs. The product, 1,2-bis(1,2,4,5-dihydroxyiminebicyclo[2.2.1]heptane)-ethyl sulfonate (82) is obtained on acidification with 6% acetic acid.

Example 12

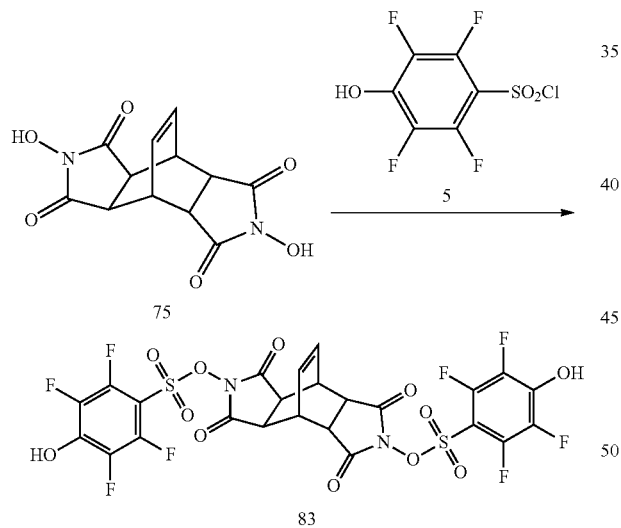

1,2-Bis(1,2,4,5-dihydroxyiminebicyclo[2.2.1]heptane)-2,3,5,6-tetrafluoro-4-hydroxybenzene sulfonate (83): The PAG-diol is made in the following manner. One equivalent of N,N'-3a,4,4a,7a,8,8a-hexahydro-2,6-dihydroxy-4,8-ethenobenzo[1,2-c:4,5-c']dipyrrole-1,3,5,7(2H,6H)-tetrone (75), is heated with two equivalents of 2,3,5,6-tetrafluoro-4-hydroxybenzene-1-sulfonyl chloride (5) in presence of anhydrous pyridine at 100° C. for 15 hrs. The product, 1,2-bis(1,2,4,5-dihydroxyiminebicyclo[2.2.1]heptane)-2,3,5,6-tetrafluoro-4-hydroxybenzene sulfonate (83) is obtained on acidification with 6% acetic acid.

Example 13

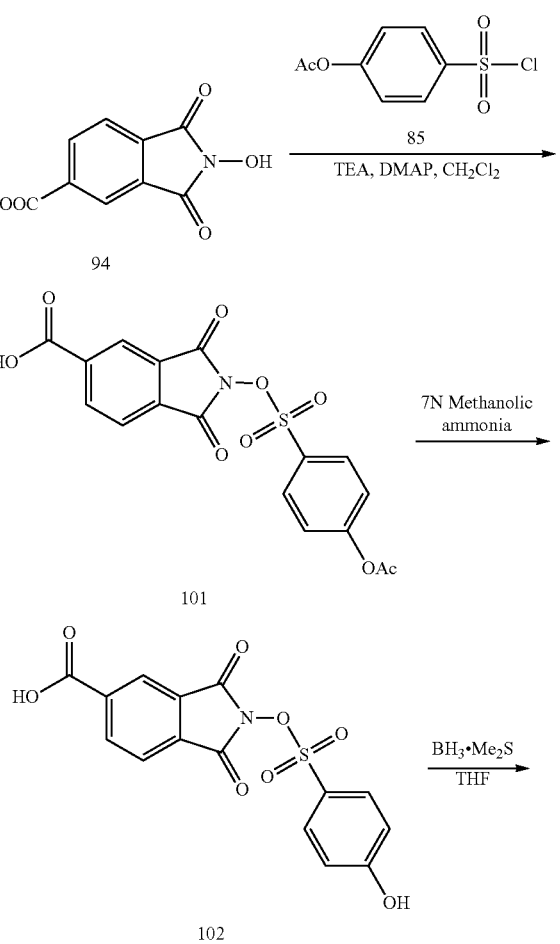

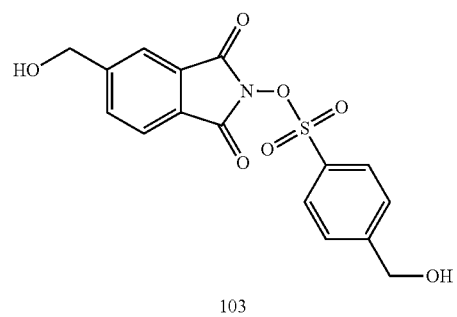

103

5-(Hydroxymethyl)-1,3-dioxoisoindolin-2-yl-4-hydroxybenzenesulfonate (103) is made in the following manner: The N-hydroxyphthalimide 4-carboxylic acid (94), made from trimellitic anhydride (93) is reacted with p-acetoxybenzene sulfonyl chloride (85) to get the corresponding p-acetoxy sulfonate (101), which on hydrolysis will give the phenol (102). The carboxylic acid group of the phenol (102) is subsequently reduced to its alcohol to get the 5-(hydroxymethyl)-1,3-dioxoisoindolin-2-yl-4-hydroxybenzenesulfonate (103).

Example 14

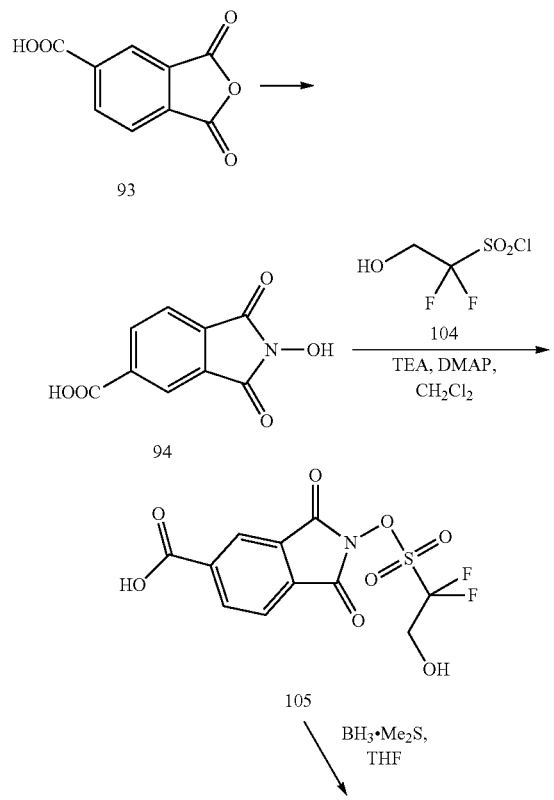

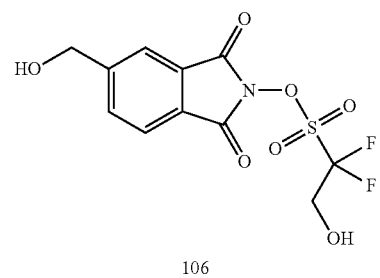

106

5-(Hydroxymethyl)-1,3-dioxoisoindolin-2-yl 1,1-difluoro-2-hydroxyethanesulfonate (106) is made in the following manner: The N-hydroxyphthalimide 4-carboxylic acid (94), made from trimelllitic anhydride (93) is converted to the corresponding 1,1-difluoro-2-hydroxyethane sulfonate (105) by reacting with 1,1-difluoro-2-hydroxyethane sulfonyl chloride (104) in presence of triethylamine and a catalytic amount of DMAP and methylene chloride. The acid (105) is then reduced to its corresponding alcohol to get the 5-(hydroxymethyl)-1,3-dioxoisoindolin-2-yl 1,1-difluoro-2-hydroxyethanesulfonate (106).

Example 15

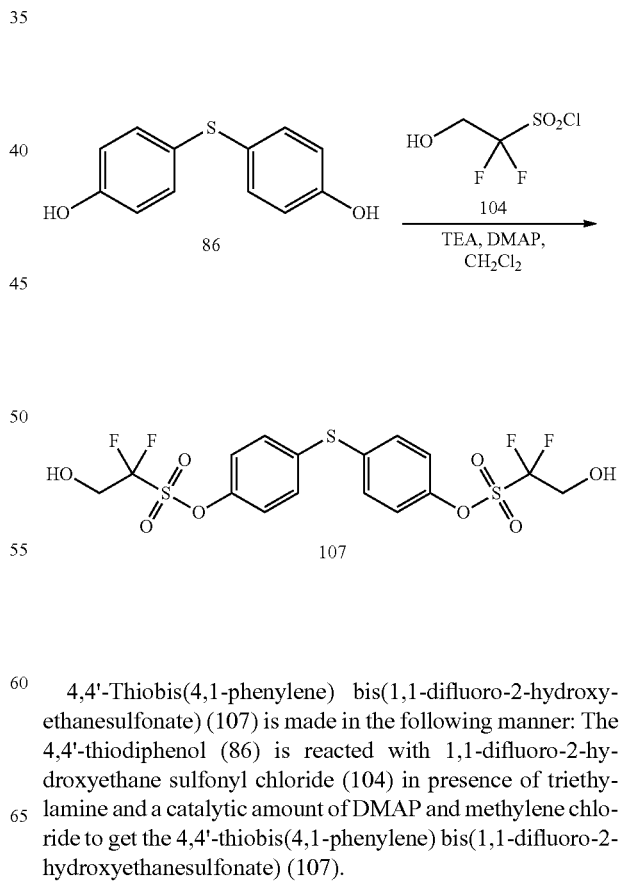

4,4'-Thiobis(4,1-phenylene) bis(1,1-difluoro-2-hydroxyethanesulfonate) (107) is made in the following manner: The 4,4'-thiodiphenol (86) is reacted with 1,1-difluoro-2-hydroxyethane sulfonyl chloride (104) in presence of triethylamine and a catalytic amount of DMAP and methylene chloride to get the 4,4'-thiobis(4,1-phenylene) bis(1,1-difluoro-2-hydroxyethanesulfonate) (107).

Example 16
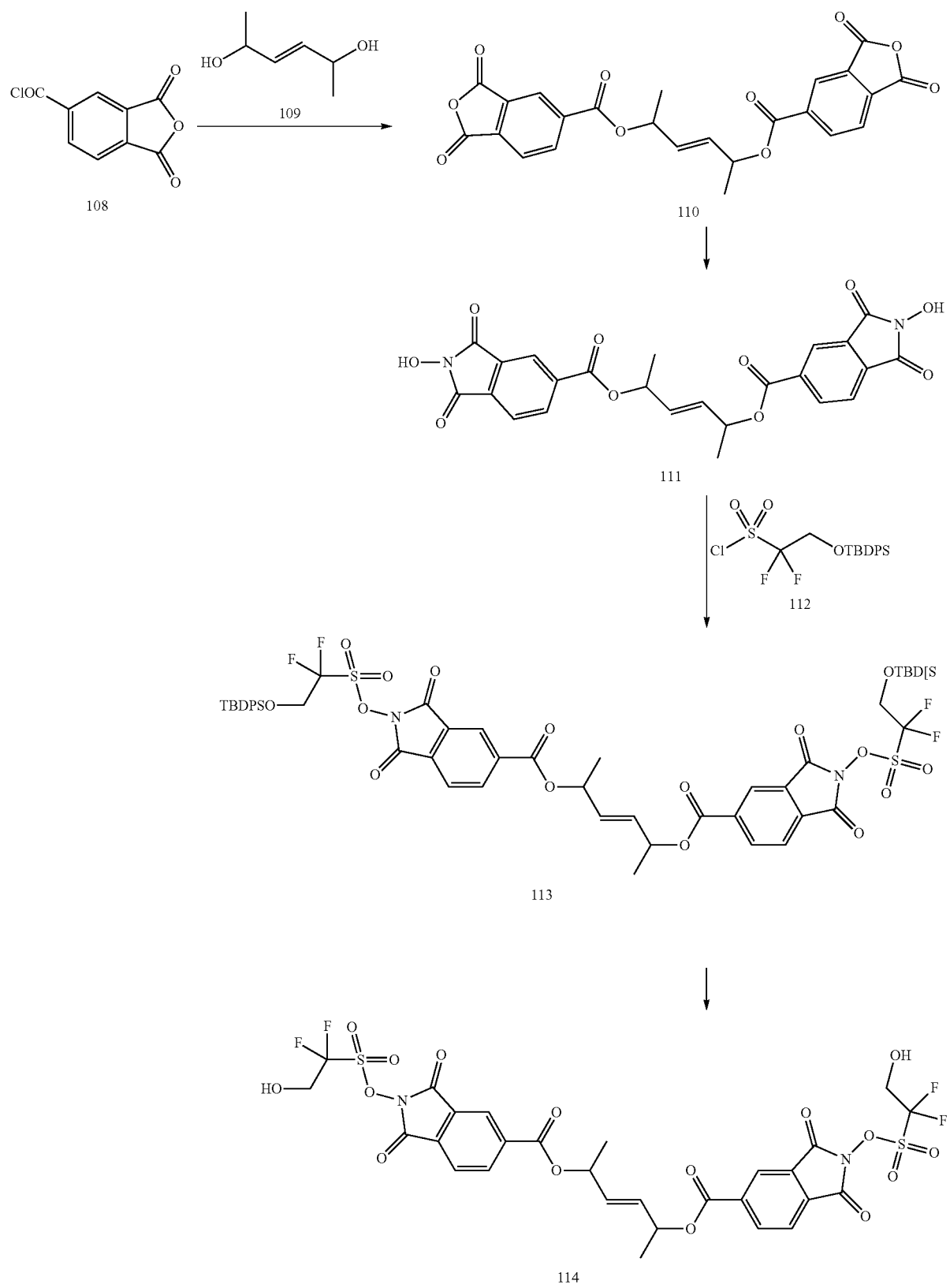

(E)-Hex-3-ene-2,5-diyl-bis(2-(1,1-difluoro-2-hydroxy-ethylsulfonyloxy)-1,3-dioxoisoindoline-5-carboxylate) (114) is made in the following manner: The trimellitic acid chloride (108) is reacted with (E)-hex-3-ene-2,5-diol (109) to get the dianhydride (110). The dianhydride is converted to the N-dihydroxydiimide (111), which is subsequently converted to the protected sulfonate (113), by reacting with the protected sulfonyl chloride (112). The protected sulfonate (113) is then deprotected to get the (E)-hex-3-ene-2,5-diyl bis(2-(1,1-difluoro-2-hydroxyethylsulfonyloxy)-1,3-dioxoisoindoline-5-carboxylate) (114).

The following monomers can be made by processes analogous to those set forth above.

Example 17

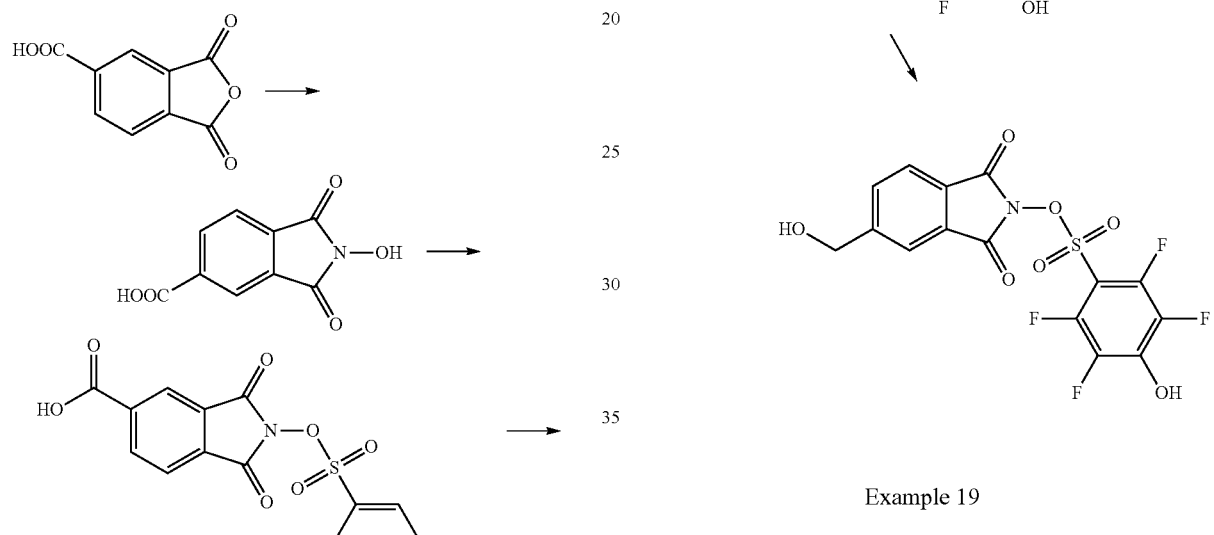

Example 18

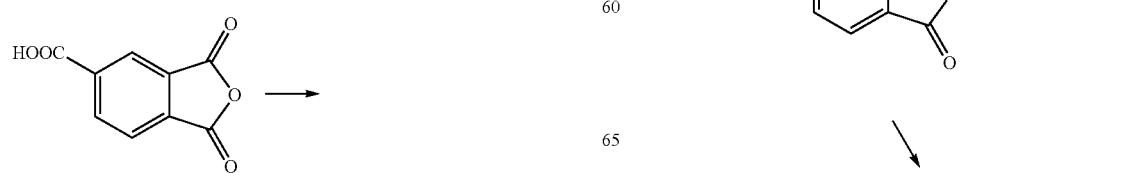

-continued

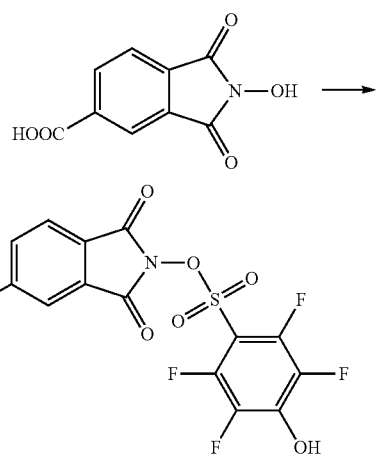

Example 19

41
-continued
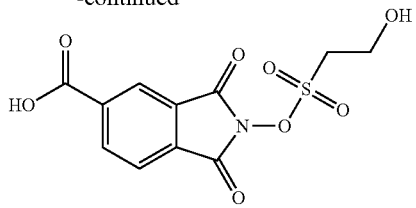
Example 20
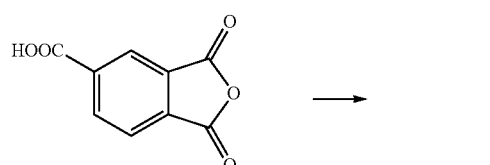
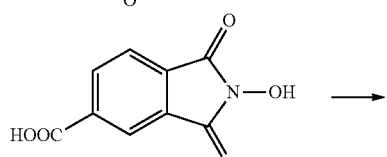
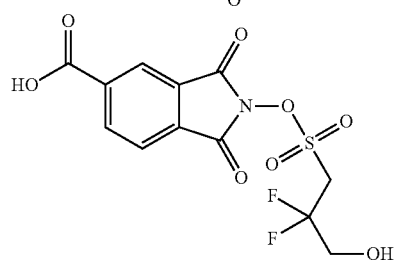
Example 21
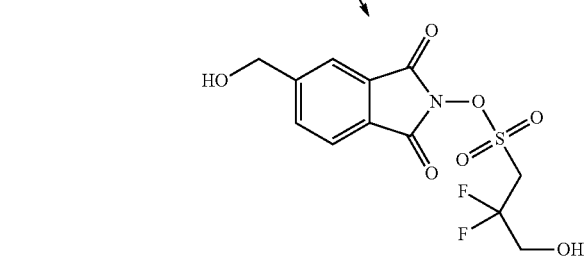
42
-continued
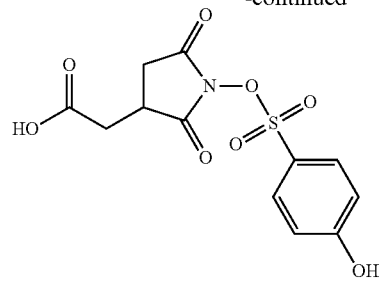
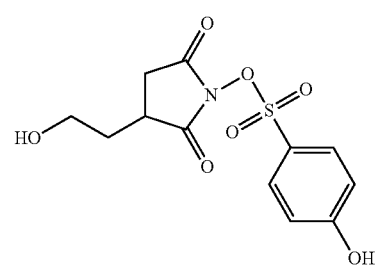
Example 22
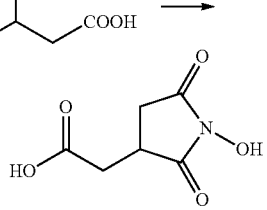
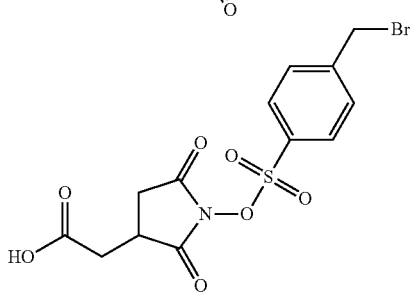
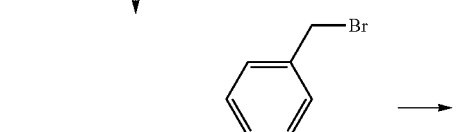
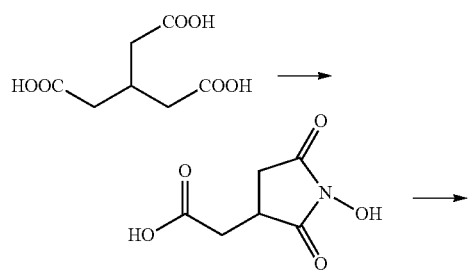

43
-continued
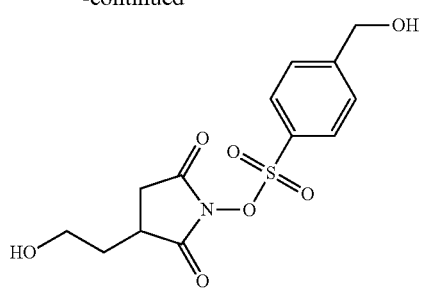
Example 23
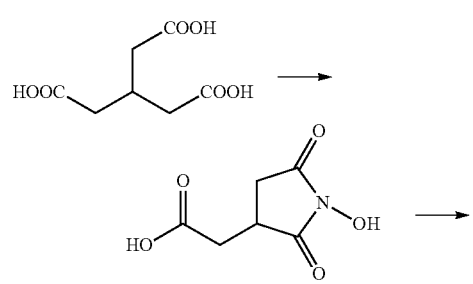
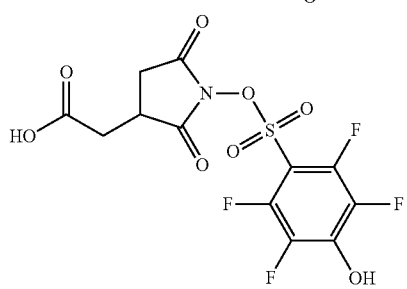
Example 24
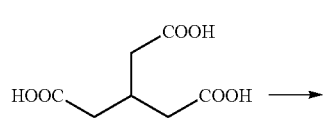
44
-continued
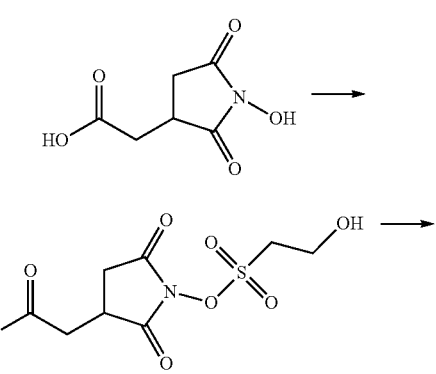
Example 25
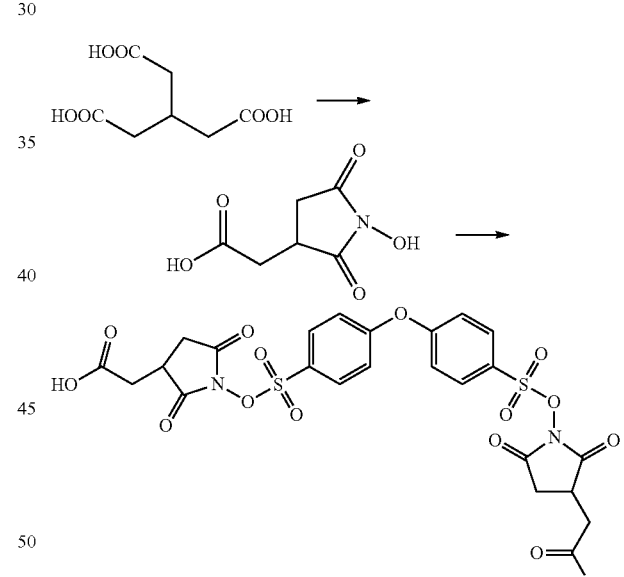
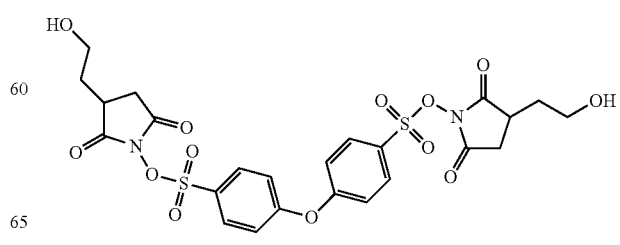

45
Example 26
46
Example 27
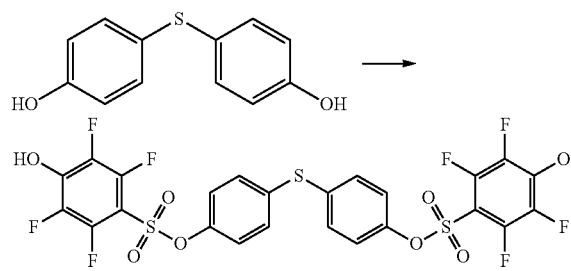
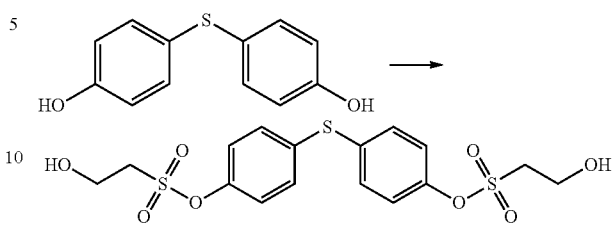
Example 28
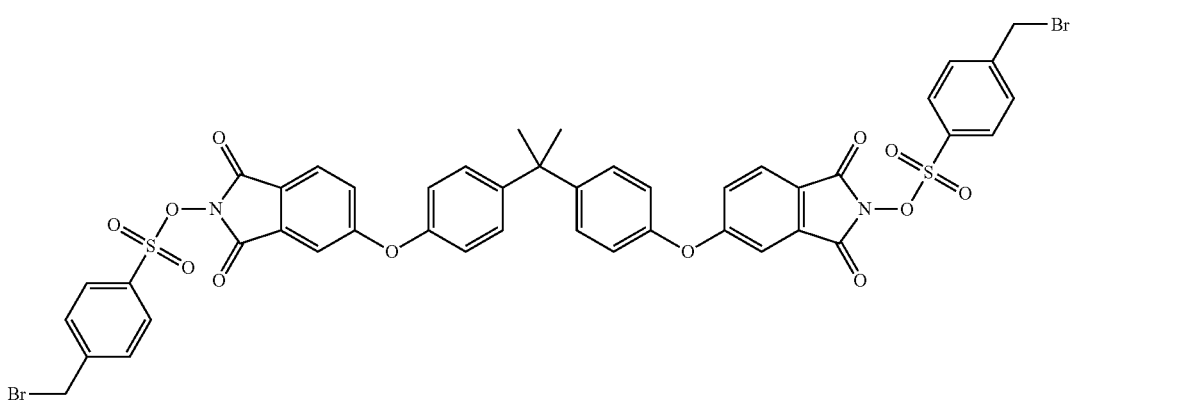
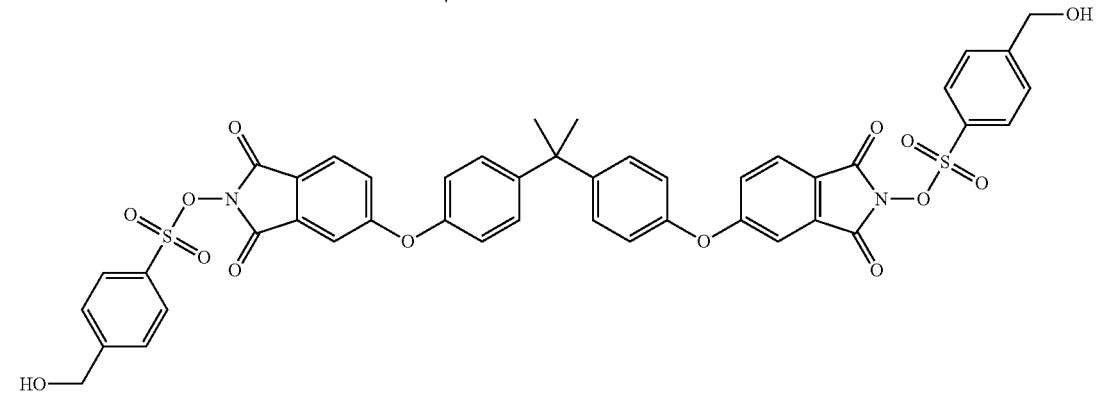
Example 29
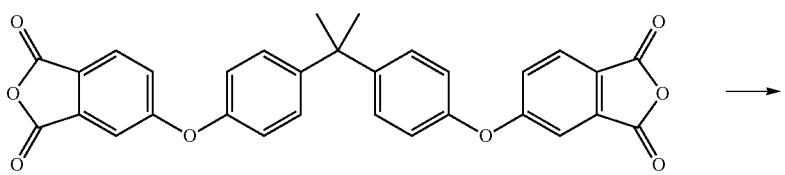

47    48
-continued
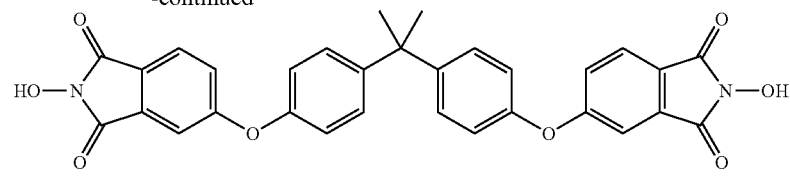
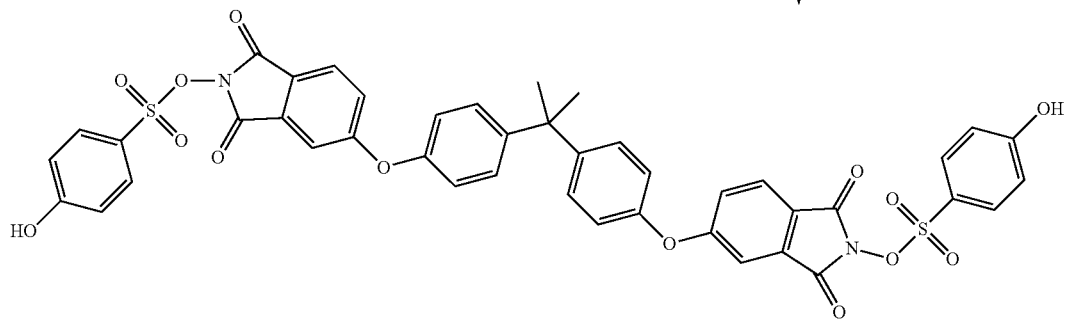
25
Example 30
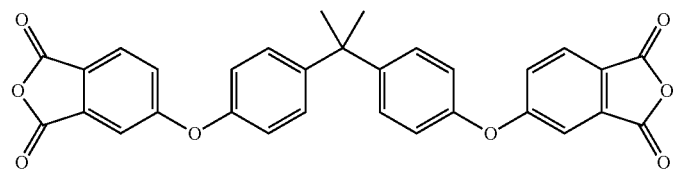
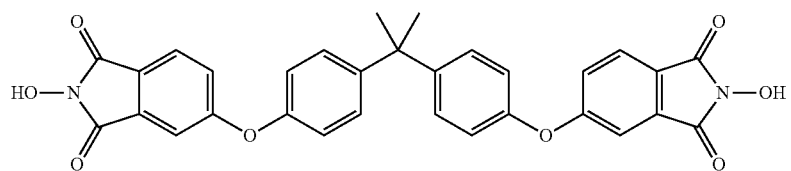
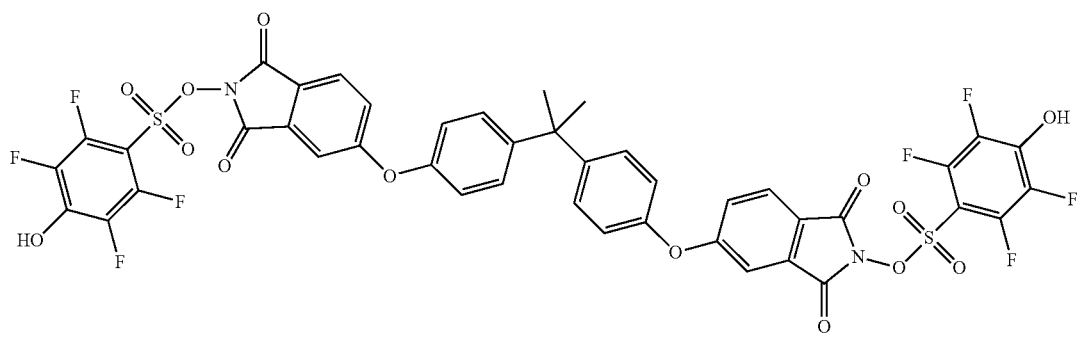

49 50
Example 31
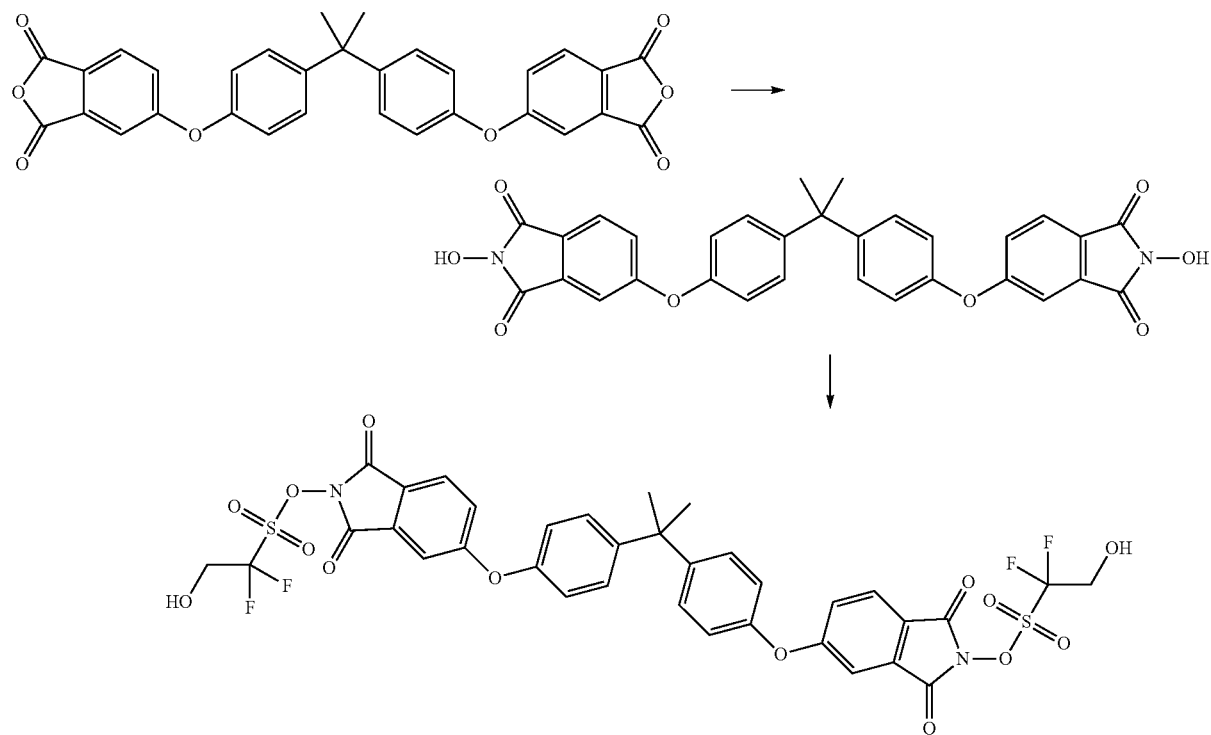
Example 32
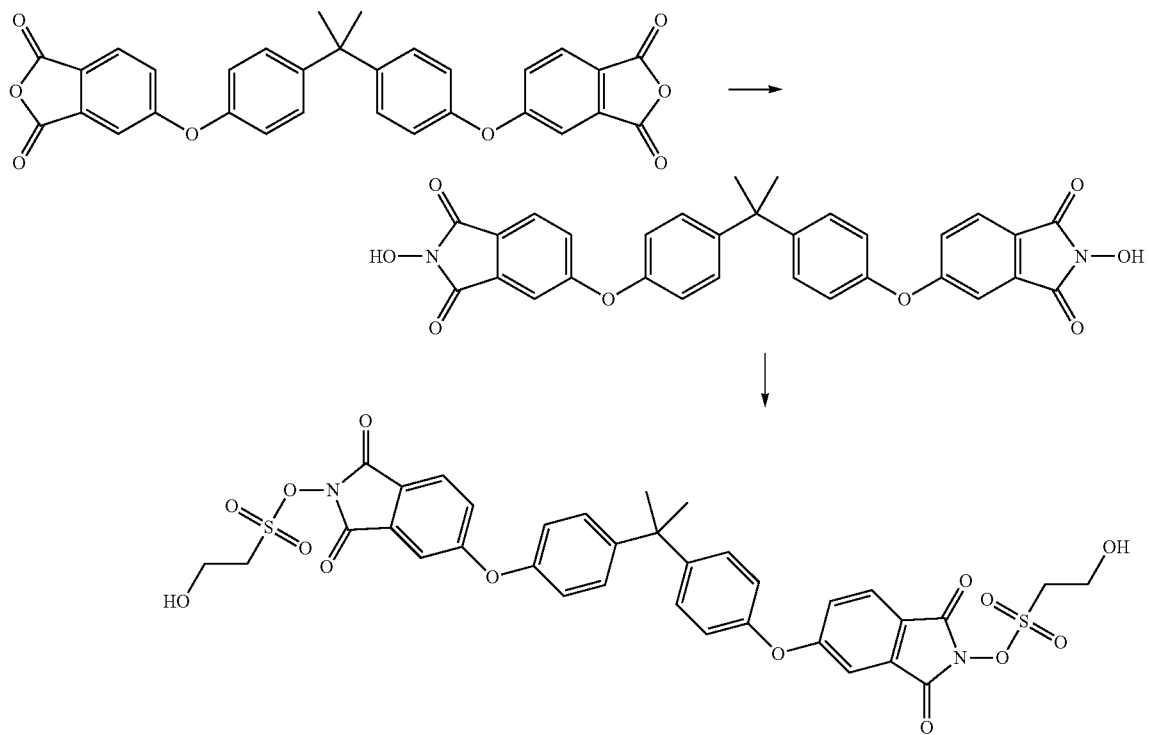

One may obtain the following monomers in similar fashion:
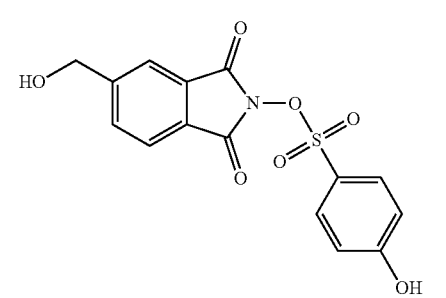
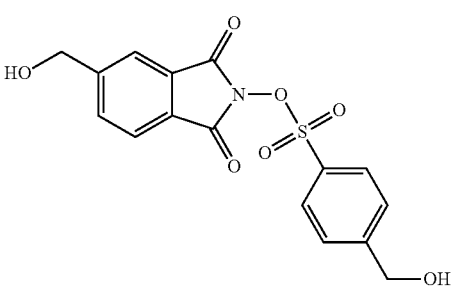
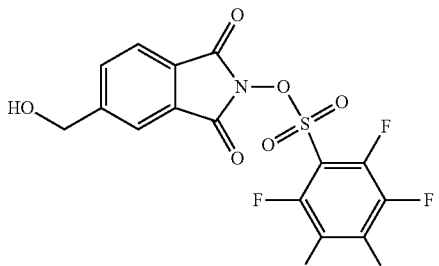
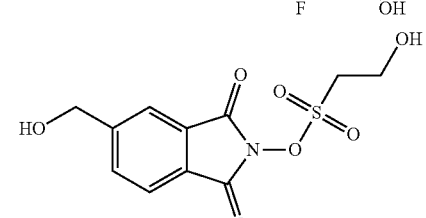
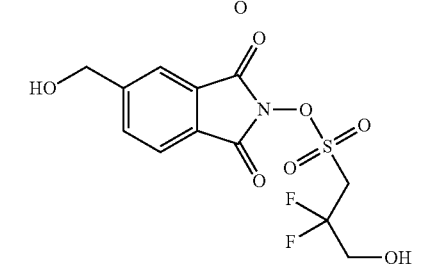
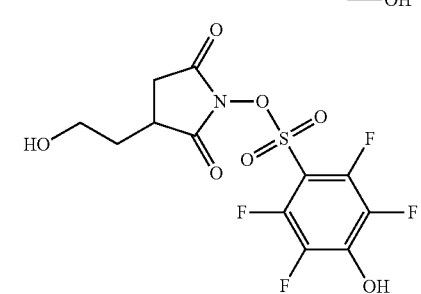
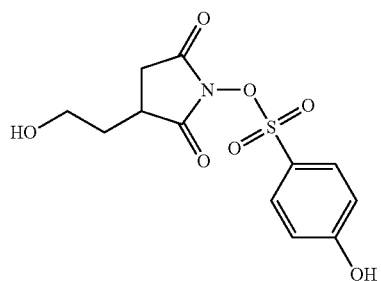
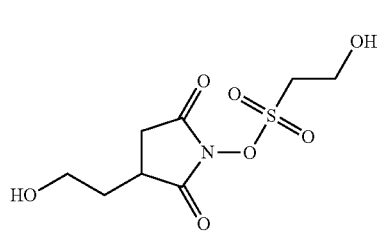
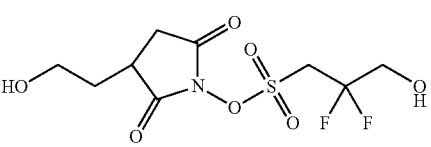
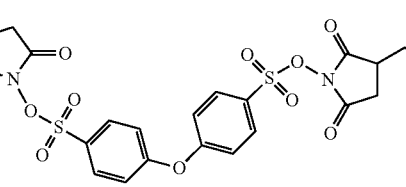
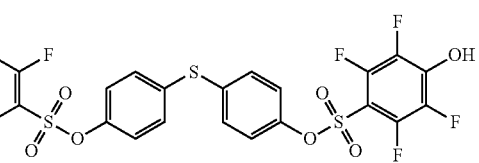
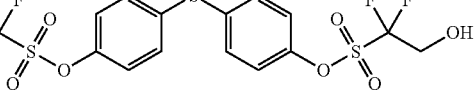
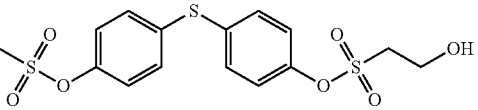
Polymerization

Example 33

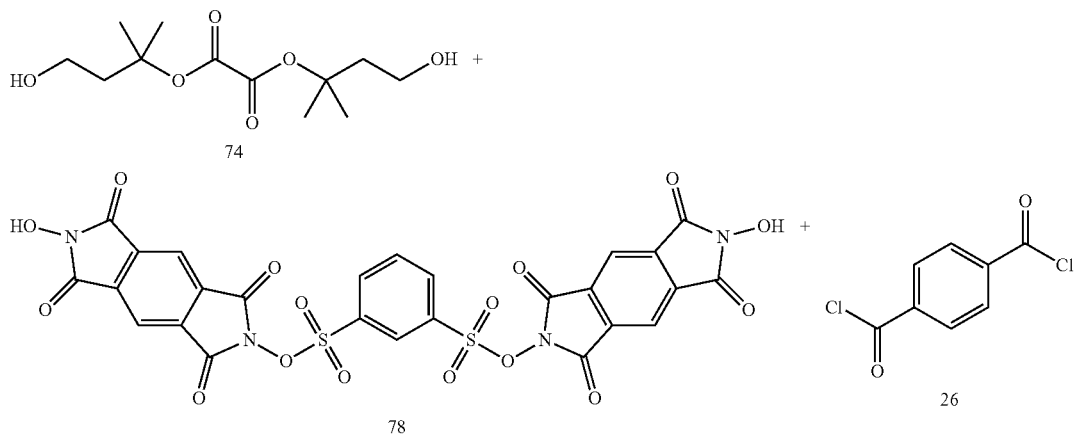

To get the polymer, nine equivalents of the cleavable diol, bis(4-hydroxy-2-methylbutan-2-yl) oxalate (74), 1 equivalent of the PAG diol, bis(6-hydroxy-1,3,5,7-tetraoxo-6,7-dihydropyrrolo[3,4-f]isoindol-2(1H,3H,5H)-yl)benzene-1,3-disulfonate (78), and 10 equivalent of pyridine are combined and dissolved in acetone. A catalytic amount of 1,4-Diazabicyclo[2.2.2]octane and potassium iodide are added and the solution is stirred and warmed to reflux. Over the course of 6 hours, 10 equivalents of terephthaloyl chloride (26) dissolved in acetone are added drop wise using a syringe pump and the solution is allowed to stir for an additional hour. Finally the reaction is quenched with ethylene diamine and precipitated out in water to give the final product.

Example 34

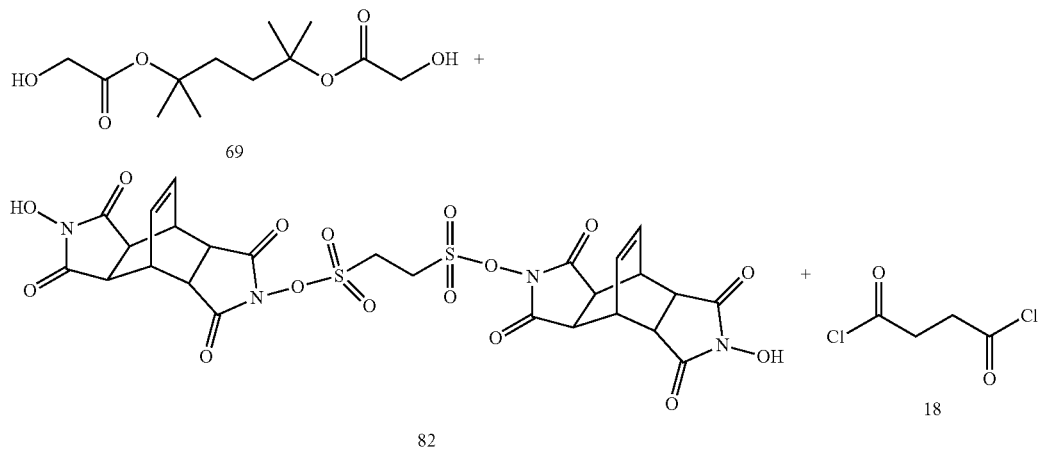

To get the polymer, nine equivalents of the cleavable diol, 2,5-dimethylhexane-2,5-diyl bis(2-hydroxyacetate) (69), 1 equivalent of the PAG diol, 1,2-bis(1,2,4,5-dihydroxyiminebicyclo[2.2.1]heptane)-ethyl sulfonate (82) and 10 equivalents of pyridine, are combined and dissolved in acetone. A catalytic amount of 1,4-Diazabicyclo[2.2.2]octane and potassium iodide are added and the solution is stirred and warmed to reflux. Over the course of 6 hours, 10 equivalents of succinyl dichloride (18) dissolved in acetone are added drop wise using a syringe pump and the solution is allowed to stir for an additional hour. Finally the reaction is quenched with ethylene diamine and precipitated out in water to give the final product.

In employing the polymers as photoresists, the molecular weight of the polymers is optimized based on the type of chemistry used and on the lithographic performance desired. Typically, the weight average molecular weight is in the range of 3,000 to 40,000 and optimally 7,000 to 20,000. The polydispersity is in the range 1.1 to 5, preferably 1.5 to 3.

In a photoresist, the solid components of the present invention are dissolved in an organic solvent. The amount of solids in the solvent or mixture of solvents ranges from about 2 weight % to about 30 weight %. The polymer may be in the range of 5 weight % to 100 weight % of the solids; usually the polymer will be in the range of 50 weight % to 99 weight % of the solids. Suitable solvents for such photoresists may include a glycol ether such as ethyl cellosolve, methyl cellosolve, propylene glycol monomethyl ether, diethylene glycol monomethyl ether, diethylene glycol monoethyl ether, dipropylene glycol dimethyl ether, propylene glycol n-propyl ether, or diethylene glycol dimethyl ether; a glycol ether ester such as ethyl cellosolve acetate, methyl cello solve acetate, or propylene glycol monomethyl ether acetate; a carboxylate such as ethyl acetate, n-butyl acetate and amyl acetate; a carboxylate of a di-basic acid such as diethyloxylate or diethylmalonate; a dicarboxylates of a glycol such as ethylene glycol diacetate and propylene glycol diacetate; a hydroxy carboxylate such as methyl lactate, ethyl lactate, ethyl glycolate, and ethyl-3-hydroxy propionate; a ketone ester such as methyl pyruvate or ethyl pyruvate; an alkoxycarboxylic acid ester such as methyl 3-methoxypropionate, ethyl 3-ethoxypropionate, ethyl 2-hydroxy-2-methylpropionate, or methylethoxypropionate; a ketone such as methyl ethyl ketone, acetyl acetone, cyclopentanone, cyclohexanone or 2-heptanone; a ketone ether such as diacetone alcohol methyl ether; a ketone alcohol such as acetol or diacetone alcohol; a lactone such as butyrolactone; an amide derivative such as dimethylacetamide or dimethylformamide, anisole, and mixtures thereof.

Various other additives such as colorants, non-actinic dyes, anti-striation agents, plasticizers, adhesion promoters, dissolution inhibitors, coating aids, photospeed enhancers, and solubility enhancers (for example, certain small levels of solvents not used as part of the main solvent examples of which include glycol ethers and glycol ether acetates, valerolactone, ketones, lactones, and the like), and surfactants may be added to the photoresist composition before the solution is coated onto a substrate. Surfactants that improve film thickness uniformity, such as fluorinated surfactants, can be added to the photoresist solution. A sensitizer that transfers energy from a particular range of wavelengths to a different exposure wavelength may also be added to the photoresist composition. Often quencher bases are also added to the photoresist to give better chemical contrast, to give better LWR and/or to prevent t-tops or bridging at the surface of the photoresist image. Examples of bases are amines, ammonium hydroxide, and photosensitive bases. Common bases are trioctylamine, diethanolamine and tetrabutylammonium hydroxide. In the case in which the CSP$^3$ polymer is intended for 193 nm, it may be found useful to incorporate a surface modification agent for immersion lithography. Examples are found in Irie et al., *Journal of Photopolymer Science and Technology* (2006), 19(4), 565-568.

The prepared photoresist composition solution can be applied to a substrate by any conventional method known in the photoresist art, including dipping, spraying, and spin coating. When spin coating, for example, the photoresist solution can be adjusted with respect to the percentage of solids content, in order to provide coating of the desired thickness, given the type of spinning equipment utilized, spinning speed and the amount of time allowed for the spinning process. Suitable substrates include silicon, aluminum, polymeric resins, silicon dioxide, doped silicon dioxide, silicon nitride, tantalum, copper, polysilicon, ceramics, aluminum/copper mixtures; gallium arsenide and other such Group III/V compounds. The photoresist may also be coated over antireflective coatings.

The photoresist coatings produced by the described procedure are particularly suitable for application to silicon/silicon dioxide wafers, such as are utilized in the production of microprocessors and other miniaturized integrated circuit components. An aluminum/aluminum oxide wafer can also be used. The substrate may also comprise various polymeric resins, especially transparent polymers such as polyesters.

The photoresist composition solution is then coated onto the substrate, and the substrate is treated at a temperature from about 70° C. to about 150° C. for from about 30 seconds to about 180 seconds on a hot plate or for from about 15 to about 90 minutes in a convection oven. This temperature treatment is selected in order to reduce the concentration of residual solvents in the photoresist, while not causing substantial thermal degradation of the solid components. In general, one desires to minimize the concentration of solvents at this first temperature. Treatment is conducted until substantially all of the solvents have evaporated and a thin coating of photoresist composition, on the order of half a micron (micrometer) in thickness, remains on the substrate. In a preferred embodiment the temperature is from about 95° C. to about 130° C. The treatment is conducted until the rate of change of solvent removal becomes relatively insignificant. The film thickness, temperature and time selection depends on the photoresist properties desired by the user, as well as the equipment used and commercially desired coating times. The coated substrate can then be imagewise exposed to actinic radiation, e.g., ultraviolet radiation, at a wavelength of from about 100 nm (nanometers) to about 300 nm, x-ray, electron beam, ion beam or laser radiation, in any desired pattern, produced by use of suitable masks, negatives, stencils, templates, and the like, etc.

The photoresist is then subjected to a post exposure second baking or heat treatment before development. The heating temperatures may range from about 90° C. to about 150° C., more preferably from about 90° C. to about 130° C. The heating may be conducted for from about 30 seconds to about 2 minutes, more preferably from about 60 seconds to about 90 seconds on a hot plate or about 30 to about 45 minutes by convection oven.

The exposed photoresist-coated substrates are developed by single or double puddle development on a track. Additional development techniques may include immersion in a developing solution or developing by spray development process. The solution is preferably agitated, for example, by nitrogen burst agitation. The substrates are allowed to remain in the developer until all, or substantially all, of the photoresist coating has dissolved from the exposed areas. Developers include aqueous solutions of ammonium or alkali metal hydroxides. After removal of the coated wafers from the developing solution, wafers are rinsed with water and then spin dried. Additionally, one may conduct an optional post-development heat treatment or bake to increase the coating's adhesion and chemical resistance to etching conditions and other substances. The post-development heat treatment can comprise the oven baking of the coating and substrate below the coating's softening point or UV hardening process. In industrial applications, particularly in the manufacture of microcircuitry units on silicon/silicon dioxide-type substrates, the developed substrates may be treated with a buffered, hydrofluoric acid base etching solution or dry etching. Prior to dry etching the photoresist may be treated to electron beam curing in order to increase the dry-etch resistance of the photoresist.

I claim:
1. A monomer of the formula

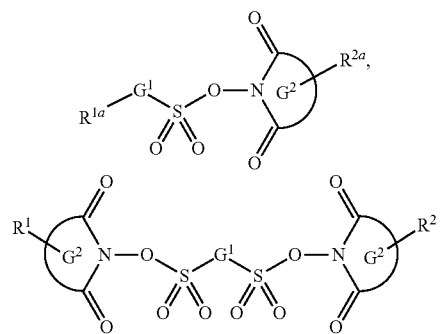

-continued

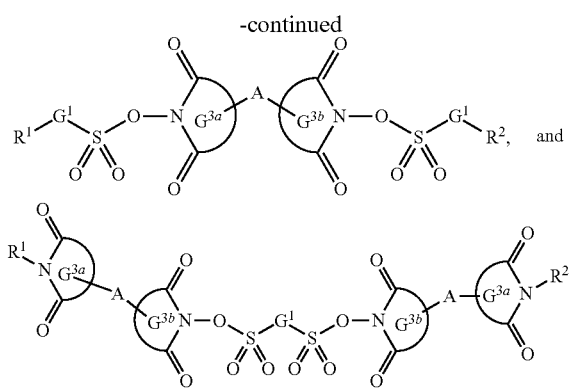

and

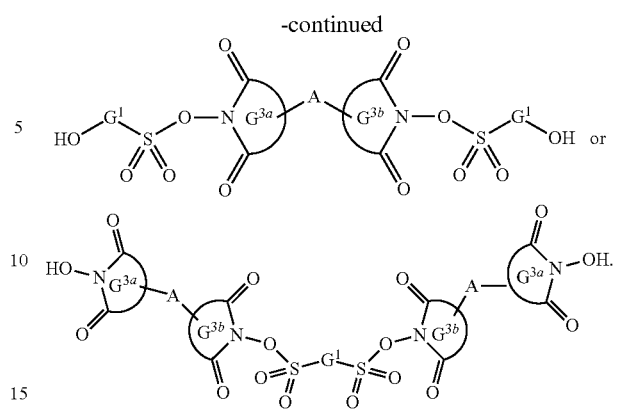

wherein
G$^1$ is selected from an alkylene, a fluoroalkylene, an arene, a fluoroarene, a benzyl, a fluorobenzyl, a diaryl ether and a diaryl;
G$^2$ is an imide of empirical formula C$_{4-20}$H$_{3-12}$N$_{1-2}$O$_{2-5}$ of which C$_2$O$_2$N is shown in the formula above;
G$^{3a}$ and G$^{3b}$ are 5- or 6-membered monocyclic or bicyclic imides of which the imide portion, C$_2$O$_2$N, is shown in the formula above;
A is a linker of empirical formula C$_{0-12}$H$_{0-8}$F$_{0-8}$N$_{0-2}$O$_{0-2}$ or

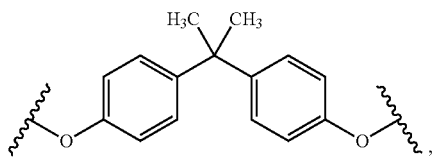 [SMILES: *Oc1ccc(C(C)(C)c2ccc(O*)cc2)cc1]

joining rings G$^{3a}$ and G$^{3b}$;
R$^1$ and R$^2$ are chosen independently from —OH, —NH$_2$, —Cl, —Br, —SO$_2$Cl, —N=C=O and —COCl;
R$^{1a}$ is chosen from —OH, —NH$_2$, —Cl, —Br, —N=C=O and —COCl; and
R$^{2a}$ is chosen from —NH$_2$, —Cl, —Br, —SO$_2$Cl, —N=C=O and —COCl.

2. A monomer according to claim 1 of formula

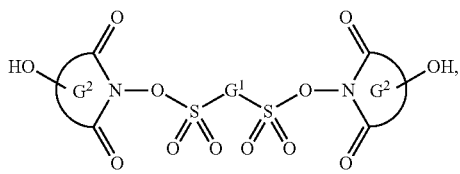

3. A monomer according to claim 1 wherein G$^1$ is selected from phenyl, (C$_2$-C$_6$)alkylene, fluorophenyl, fluoro(C$_2$-C$_6$)alkylene, benzyl, biphenyl and diphenyl ether.

4. A monomer of formula

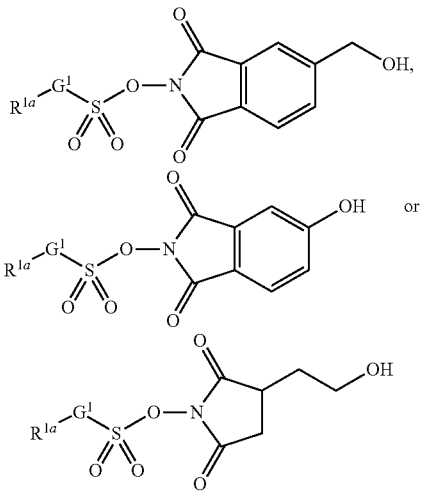

wherein
G$^1$ is selected from an alkylene, a fluoroalkylene, an arene, a fluoroarene, a benzyl, a fluorobenzyl, a diaryl ether and a diaryl; and
R$^{1a}$ is chosen from —OH, —NH$_2$, —Cl, —Br, —N=C=O and —COCl.

* * * * *